(12) United States Patent
Overbeck

(10) Patent No.: US 6,335,824 B1
(45) Date of Patent: Jan. 1, 2002

(54) WIDE FIELD OF VIEW AND HIGH SPEED SCANNING MICROSCOPY

(75) Inventor: James W. Overbeck, Hingham, MA (US)

(73) Assignee: Genetic Microsystems, Inc., Woburn, MA (US)

( * ) Notice: Subject to any disclaimer, the term of this patent is extended or adjusted under 35 U.S.C. 154(b) by 0 days.

(21) Appl. No.: 09/665,544

(22) Filed: Sep. 19, 2000

Related U.S. Application Data

(63) Continuation of application No. PCT/US99/06097, filed on Mar. 19, 1999, which is a continuation-in-part of application No. 09/170,847, filed on Oct. 13, 1998, which is a continuation-in-part of application No. 09/045,547, filed on Mar. 20, 1998.

(51) Int. Cl.$^7$ .................. G02B 21/00; G02B 26/08; G02B 21/02; G02B 7/02

(52) U.S. Cl. ............... 359/368; 359/210; 359/813; 359/656

(58) Field of Search .................. 359/210, 201, 359/806, 813, 381, 656, 661, 368; 369/44.17, 44.18, 44.19, 44.21

(56) References Cited

U.S. PATENT DOCUMENTS

| | | |
|---|---|---|
| 3,013,467 A | 12/1961 | Minsky .................. 88/14 |
| 3,588,218 A | 6/1971 | Hunt et al. |
| 3,643,015 A | 2/1972 | Davidovits et al. .......... 178/6.8 |
| 3,704,372 A | 11/1972 | Parker et al. |
| 3,879,615 A | 4/1975 | Moser |
| 3,891,299 A | 6/1975 | Rushing .................. 350/6 |
| 3,952,217 A | 4/1976 | Rawlings ................ 310/36 |
| 3,967,114 A | 6/1976 | Cornillault |
| 4,087,685 A | 5/1978 | Froot ................... 250/302 |
| 4,168,126 A | 9/1979 | Altman et al. ........... 356/386 |
| 4,289,371 A | 9/1981 | Kramer |

(List continued on next page.)

FOREIGN PATENT DOCUMENTS

| | | |
|---|---|---|
| DE | 40 20 527 C2 | 1/1992 |
| EP | 0 277 675 | 8/1988 |
| WO | WO 88/02846 | 4/1988 |
| WO | WO 96/18205 | 6/1996 |
| WO | WO 96/36062 | 11/1996 |
| WO | WO 97/28439 | 8/1997 |

OTHER PUBLICATIONS

Beiser, Leo, "Laser Scanning and Recording: Developments and Trends", *Laser* Focus, (1985).

Castellino, Alexander M., "When the Chips are Down", *Genome Research*, vol. 7, No. 10, (1997).

White, D.L., "Soft X–ray Projection Lighography", *Solid State Technology*, (1991).

"The Infrared Handbook", *The Infrared Information Analysis (IRIA) Center*, 1989.

(List continued on next page.)

Primary Examiner—Cassandra Spyrou
Assistant Examiner—Jared Treas
(74) Attorney, Agent, or Firm—Philip L. McGarrigle; Alan B. Sherr; Ivan D. Zitkovsky

(57) ABSTRACT

Limited rotation, micro-lens scanning of DNA arrays, microscope slides, biological materials, etc., is performed by arcuate and translational motion. A scanning system includes an objective lens located on a low moment of inertia oscillating arm, which provides optical coupling to a light source or a light detector arranged for transmission, reflection, or fluorescence microscopy.

35 Claims, 13 Drawing Sheets

U.S. PATENT DOCUMENTS

| | | | |
|---|---|---|---|
| 4,301,374 A | 11/1981 | Hashiue | |
| 4,322,063 A | 3/1982 | Fishbeck et al. | 267/160 |
| 4,323,307 A | 4/1982 | Seeley | 355/51 |
| 4,379,624 A | 4/1983 | Miller et al. | |
| 4,413,180 A | 11/1983 | Libby | |
| 4,525,030 A | 6/1985 | Montagu et al. | 350/255 |
| 4,532,426 A | 7/1985 | Reeds | 250/442.1 |
| 4,567,585 A | 1/1986 | Gelbart | 369/97 |
| 4,611,881 A | 9/1986 | Schmidt et al. | |
| 4,631,581 A | 12/1986 | Carlsson | |
| 4,684,797 A | 8/1987 | Ando et al. | |
| 4,712,887 A | 12/1987 | Baer | |
| 4,718,050 A * | 1/1988 | Kurz et al. | 369/44.16 |
| 4,761,774 A * | 8/1988 | Ishibashi et al. | 369/44.19 |
| 4,784,481 A | 11/1988 | Wuerfel | 350/529 |
| 4,861,144 A | 8/1989 | Russell | 350/412 |
| 4,877,966 A | 10/1989 | Tomei et al. | |
| 4,881,812 A | 11/1989 | Ohkubo et al. | 356/344 |
| 4,886,968 A | 12/1989 | Ohnishi | |
| 4,995,711 A | 2/1991 | Imai et al. | 350/529 |
| 5,001,694 A | 3/1991 | Lee et al. | |
| 5,029,955 A | 7/1991 | Chu | |
| 5,074,628 A | 12/1991 | Khattak et al. | 359/205 |
| 5,088,079 A | 2/1992 | Baer | |
| 5,091,652 A | 2/1992 | Mathies et al. | |
| 5,143,854 A | 9/1992 | Pirrung et al. | 436/518 |
| 5,171,984 A | 12/1992 | van Rosmalen | 250/236 |
| 5,193,013 A | 3/1993 | Swanberg | 358/481 |
| 5,195,074 A | 3/1993 | Tanoshima et al. | |
| 5,216,247 A | 6/1993 | Wang et al. | |
| 5,224,088 A | 6/1993 | Atiya | |
| 5,274,240 A | 12/1993 | Mathies et al. | |
| 5,293,363 A | 3/1994 | Takeshita | |
| 5,315,375 A | 5/1994 | Allen | 356/417 |
| 5,381,224 A | 1/1995 | Dixon et al. | |
| 5,424,841 A | 6/1995 | Van Gelder et al. | 356/417 |
| 5,436,718 A | 7/1995 | Fernandes et al. | 356/73 |
| 5,459,325 A | 10/1995 | Hueton et al. | |
| 5,528,050 A | 6/1996 | Miller et al. | |
| 5,535,040 A | 7/1996 | Ohtsuka et al. | 359/210 |
| 5,552,928 A | 9/1996 | Furuhashi et al. | 359/379 |
| 5,578,818 A | 11/1996 | Kain et al. | |
| 5,578,832 A | 11/1996 | Trulson et al. | |
| 5,585,639 A | 12/1996 | Dorsel et al. | 250/458.1 |
| 5,610,754 A | 3/1997 | Ghee et al. | |
| 5,631,734 A | 5/1997 | Stern et al. | |
| 5,646,411 A | 7/1997 | Kain et al. | |
| 5,650,614 A * | 7/1997 | Yasutake et al. | 250/234 |
| 5,672,880 A | 9/1997 | Kain | |
| 5,719,391 A | 2/1998 | Kain | 250/235 |
| 5,737,121 A | 4/1998 | Dixon | |
| 5,760,951 A | 6/1998 | Dixon et al. | |
| 5,800,992 A | 9/1998 | Fodor et al. | |
| 5,880,465 A | 3/1999 | Boettner et al. | 250/234 |
| 5,895,915 A | 4/1999 | DeWeerd et al. | 250/234 |
| 6,185,030 B1 | 2/2001 | Overbeck | |
| 6,027,960 A1 * | 3/2001 | Stern | 250/458.1 |

Alexay et al., "Fluorescence Scanner Employing a Macro Scanning Objective", *SPIE*, vol. 2705.

Benschop, J.P.H., "Miniature Scanning Optical Microscope Based on Compact Disc Technology", *Optical Storage and Scanning Technology*, vol. 1139, (1989).

Hamilton, D.K., "Scanning Optical Microscopy of Objective Lens Scanning", *Journal of Physics E: Scientific Instruments*, vol. 19, (1986).

Hanzel et al., "Investigation of a Microscanning Technology for the interrogation of Histological Samples", *Molecular Dynamics*, (1997).

Ishibashi, H., "High Speed accessing Magneto–Optical Disk Drive", *Optical Storage Technology and Application*, vol. 19, (1986).

Towner, David K., "Scanning Techniques for Optical data Storage", *Society of Photo–Optical Instrumentation Engineers*, vol. 695, (1986).

Yak, A.S., "High Speed Swing Arm Three Beam Optical Head", *Optical Storage Technologies*, vol. 1401, (1990).

Benschop et al., "Confocal compact scanning optical microscope based on compact disc technology" *Applied Optics*, vol. 30, No. 10 (1991); pp 1179–1184.

Dixon et al., "Confocal Scanning Beam Laser Microscope/Macroscope", *IS&T/SPIE Symposium on Electronic Imaging Science and Technology*, (1995); pp 1–10.

Montagu et al., "Fluorescence Array Scanner"; (1999); pp 1–9.

* cited by examiner

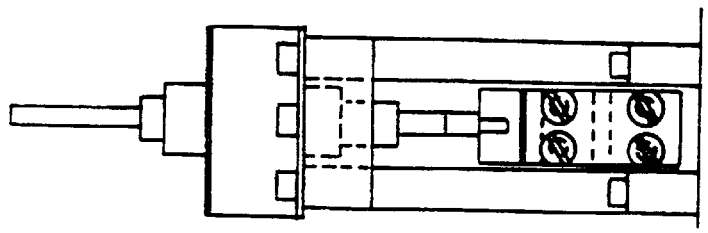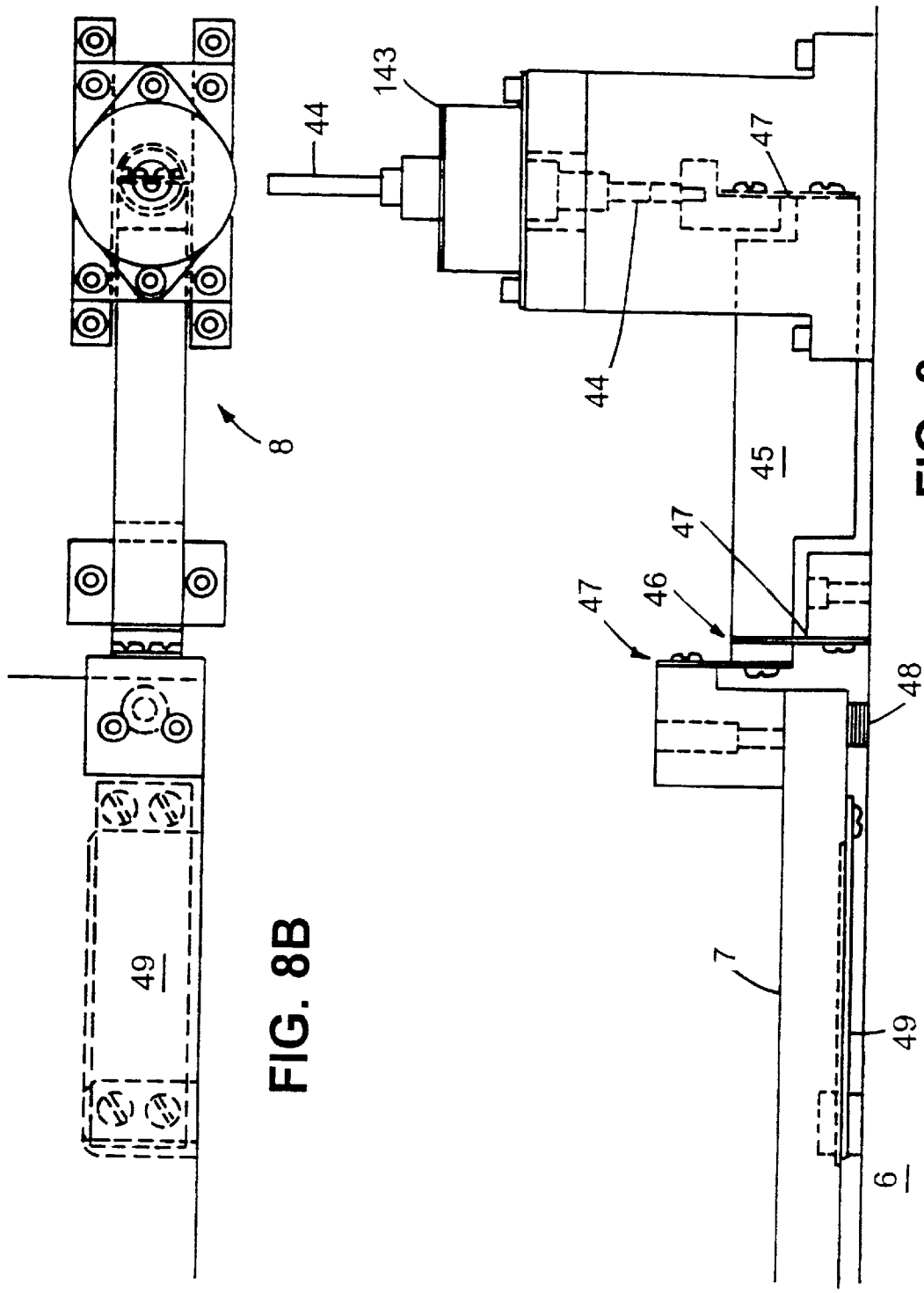

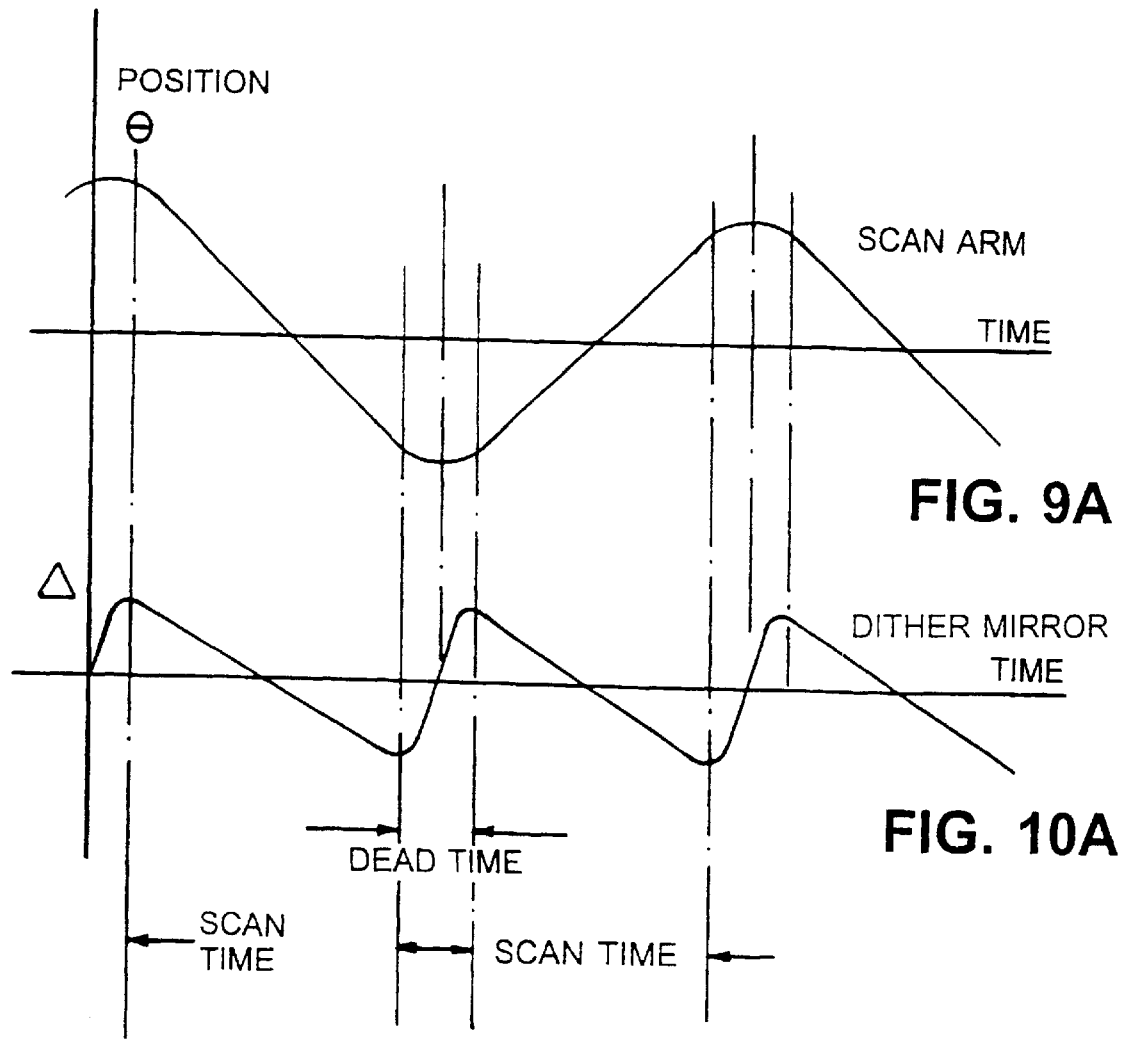

WIDE FIELD OF VIEW AND HIGH SPEED SCANNING MICROSCOPY

This application is a continuation of PCT Application PCT/US99/06097 filed on Mar. 19, 1999; which in turns is a continuation in part of U.S. Application Ser. No. 09/045,547, filed Mar. 20, 1998, entitled Wide Field of View and High Speed Scanning Microscopy, and of U.S. Application Ser. No. 09/170,847, filed Oct. 13, 1998, of the same title, which are both hereby incorporated by reference.

In microscopy for life sciences it is desirable to scan wide areas at high resolution and practical cost.

In the case of histology it is desirable to scan and store wide area views of microscope slides that carry tissue samples, cell cultures, arrays of diagnostic reagents exposed to blood, etc. Typical microscope slides have a viewable area of 2.5 cm by 7.5 cm.

In biotechnology research it is desirable to perform wide field of view microscopy of tissue cultures, DNA arrays on slides, DNA chips, segregated samples from gel electrophoresis, etc.

Such scanning is done to form images of objects, to read fluorescent emissions, or to illuminate, measure, alter or otherwise treat wide areas or discrete locations distributed over wide areas.

It is usually desirable to perform the microscopy tasks at as high a speed as possible, consistent with the amount of light that is received from the object.

Combining wide field microscopy with high speed can achieve telepathology via phone lines and satellite, more efficient evaluation of hybridization arrays, optical mapping of enzymatic restriction maps, etc.

A particularly important potential for high speed, wide field of view microscopy is the Human Genome project. By the year 2005 it is the goal to sequence the entire human genome of some 3 billion nucleotides, of which only some few million have been sequenced in the first five years of the project. The principles articulated here provide a way to speed this research.

High speed, wide area scanning, made available in a low cost system, can contribute to efficiencies in capital equipment and manpower not only in life sciences and biotechnology research, but also in the semiconductor industry and other technologies where microscopy is applicable.

According to one of the present contributions, it has been realized that wide field of view microscopy as well as high speed microscopy can be practically achieved by incorporating a micro objective lens in a limited rotation scanning structure of low moment of inertia. Where X, Y raster formats are desired the detected data from scan arcs is interpolated to equally spaced data points in an X, Y raster format. By this system images can be formed, manipulated, zoomed upon and analyzed from both macro and microscopic perspectives in a highly efficient manner. "Micro lens" as used here refers to lens assemblies weighing less than 2 grams and includes a single lens element having weight that is significantly less than 1 gram. "Micro objective" as used here refers to movable micro lenses which either constitute the objective or constitute the first part of a multi element objective in which other elements are stationary.

Rather counter-intuitively, in particular, it is found that, a "first in its class" wide field of view microscope, or high speed microscope, can be achieved by employing a limited rotation driver, or galvanometer, carrying an extremely small field of view aspheric scanning micro objective lens.

Micro lenses, and in particular, aspheric micro lenses have a basic feature by which they differ from conventional microscope objectives. They are capable of focusing only on a very small spot, whereas high magnification commercial microscope objectives that use limited rotation techniques typically focus on an area greater than 100 microns in diameter.

While it is possible for the rotationally oscillating structure that carries the micro lens to also carry its own light source, in presently preferred cases the light source and detector assemblies remain stationary and communicate with the rotating objective by a periscope assembly that involves a pair of reflectors on the rotating, low moment of inertia structure.

The rotary micro lenses can avoid aberration effects by operating on-axis, and by the use of a single or a very few micro optical lens elements in the rotating assembly. Chromatic aberration is avoided in use of such micro lenses by manipulation of the different wavelengths in the stationary portion of the optical path. The light rays of various wavelengths are brought to focus at different points in the optical path in a compensating relationship that is predetermined to offset the chromatic aberration characteristic of the micro lens.

In applications of the new techniques to fluorescence microscopy, a micro objective lens mounted for limited rotation scanning, and having a large numerical aperture, is effective to collect the low intensity fluorescing wavelength in a cost-effective manner.

While various types of illumination may be employed with microscopes employing principles that have been discussed, it is advantageous to employ laser illumination for transmission and reflectance microscopy and in fluorescence readers. The new techniques are useful with advantage in some instances with a single color laser. With multiple lasers producing two colors, or three or more colors, it is possible to make multiple passes over the object, e.g. one for each color. Advantageously, however, examination of all colors is performed simultaneously, to conduct the entire chromatic examination in one pass.

The basic idea, to employ a tiny, low mass lens, preferably an aspheric lens, mounted in a low moment of inertia, limited rotation assembly for on-axis rotational scanning structure, can employ lenses made in a number of different ways. While a commercial glass lens made for fiber optic communications by a gel molding technique developed by Corning has been proposed, for present practical cases, the rotating lens may be molded of acrylic or styrene resin using well known lens design and molding techniques and grinding, machining and polishing techniques, etc.

For many systems of interest, an effective field of view for the limited rotation scanning microscope system is at least 1 cm square and preferably 1 inch (2.5 cm) by 3 inches (7.5 cm) or, for large microscope slides or the like, 3 inches by 4 inches, or more.

Resolution to fit the microscopic need can be readily achieved. In some dermatology applications, for instance, one may be interested to view cells which are 5 or 50 microns in dimension. In this case a micro lens with one micron resolution or greater is desirable.

For most practical applications of combined wide field of view and high speed limited rotation scanning, where there is an abundance of detected radiation, the numerical aperture (NA) of the scanning objective lens element is no less than about 0.5.

In fluorescence applications, the detected light levels are lower and the considerations are different from those of imaging. NA values in excess of 0.6, and as high as the order of 0.7 or 0.8 and even 0.9, near the theoretical limit in air, are obtainable and of significant advantage. The illumination spot size in fluorescence detection is often relatively large in the preferred embodiments, between 1 and 15 microns, and the energy collection ability of the lens, related to numerical aperture, is important. A limited rotation aspheric lens with NA of 0.8 enjoys a benefit of about 3 in light collection over a lens of 0.5 numerical aperture. Thus while employing large illumination spot sizes in limited rotation fluorescence microscopy, the aspheric micro lenses with high numerical aperture are of considerable advantage in low cost, relatively high speed applications.

Another contribution presented here is the use, with the rotary scanning structure, of a stationary periscope that extends closely over the object to conduct light from the stationary source to a stationary mirror directed along the axis of rotation to a reflector on the rotary assembly, thence to the rotating objective lens.

For many applications it is advantageous to move the object continuously under the limited rotation scanning head. Another contribution presented here concerns the reduction of scan overlap inefficiencies in such a system by introducing compensating motions of the beam relative to the rotating lens. When an objective lens is oscillated in a circular arc and the object is relatively translated continuously underneath (by translation of the object or translation of the axis of the rotating structure), a generally curved triangular scan pattern occurs upon the object and the object is not scanned uniformly when the image is acquired in both cw and ccw (back and forth) scans. If, for instance, the uniform spot size is such that the spot in the center of a scan arc, aligned with the direction of the translation, touches the path of the spot in the next successive scan, the scans will overlap considerably toward the apices of the curved triangular shaped wave pattern, while in the divergent regions of the pattern, areas of the object will be missed by the scan arcs. A compensating motion is introduced to the light path in the rotary system to cause successive scan paths to have a substantially uniform spacing over their useful length. This is implemented by moving the beam radially relative to the objective lens as rotation of the objective lens occurs, the objective lens being selected to have field of view of a minimum dimension of twice or more the spot size, so that the beam remains on the lens throughout the compensating excursion. For instance for a 5 micron diameter focused spot size, an objective lens having a minimum field of view of 10 microns, plus any amount necessary to facilitate alignment, is employed.

A simple device for achieving the compensatory motion is a dithering folding mirror located in the stationary optical path that addresses the rotating structure. A piezo-electric crystal dithers the mirror in synchronization with the rotary oscillations of the arm. This causes the beam to oscillate radially on the lens as the arm rotates. Instead of a piezo electric dither mirror, other reflecting devices may be dithered, or the compensating motion may be introduced into the beam path by other means, for instance by acousto-optic deflectors, electro-optic deflectors, rotary cranks or other moving linkages driven by motors.

The dither feature may be employed in various other ways, for instance to enable multiple scans of the object while the object is stationary relative to the scan arm axis.

Another contribution presented here is an efficient interpolation scheme and algorithm that converts scanned arc data values along arcuate scan lines to the uniformly spaced points of a raster format.

The specific construction details of the presently preferred implementations are also unique, and constitute contributions to microscope technology. While low mass mirrors are preferred in the moving system it will be appreciated that other reflectors, such as prisms, may be employed and other mechanical and electronic systems can be employed using concepts presented here.

Besides biological and life science applications, certain of the concepts have application to the silicon device industry, e.g. to inspect the relationship of features of an electronic device, such as inspection for co-planarity of features on a semiconductor chip such as a ball grid array used for making electrical connections to the chip.

By combining a confocal assembly with the limited rotation microscope described, the very shallow depth of field achieved enables verification that all legs of a silicon device are co-planar, while all of the data for the entire chip is captured rapidly in one bite (one wide view scan sequence). Likewise, one may perform three-dimensional mapping of features of silicon devices, living cells, or other objects.

According to one of the contributions, in a wide field of view, limited rotation scanning microscope for examination of a surface of an object, a scanning assembly is provided which comprises an oscillating rotary support structure associated with a driver and constructed to travel in periodic motion over the object to be viewed in a predetermined arcuate scan path over a scan range of at least 1 mm, a micro objective lens mounted on the rotary oscillating support structure, the micro objective lens characterized in having weight of less than about 2 grams, the lens mounted on the support structure with its axis normal to the surface of the object for essentially on-axis scanning throughout the arcuate scan range, and the driver for the support structure adapted to oscillate the support structure to cause on-axis scanning of the object.

Preferred embodiments of this aspect have one or more of the following features.

A reflecting system is mounted on the rotary support structure to define a light path communicating with the micro lens along the axis of the lens, the reflecting system constructed to maintain this optical path in optical communication with a stationary optical system over a light path of fixed length throughout the range of travel of the rotary oscillating support structure.

The micro objective lens is an aspheric lens.

The micro objective lens forms the entire objective of the microscope or it cooperates with stationary optical elements to form the objective of the microscope.

The oscillating assembly has a moment of inertia less than 25 gm-cm$^2$.

Stationary optics produce at least two beams of different wave lengths and a merging system is constructed to merge the beams into a single illuminating beam directed to the micro objective lens. Preferably, where the micro objective lens has characteristic chromatic aberration, at least one device is included in the path of at least one of the beams to cause rays of one wave length to focus at a point different from the point of focus of rays of another wave length, the different focusing characteristics of the rays being redetermined in relation to the chromatic aberration characteristic of the objective lens to enable focus of the respective wave lengths, by the objective lens, upon the same point on the object.

Another of the contributions is a wide field of view limited rotation scanning microscope system which comprises the rotating, micro lens assembly described, combined with a translation system for producing relative linear movement over a translation range of an object to be scanned relative to the rotary support structure, the direction of translation being substantially normal to the center region of the limited rotation scan path.

Preferred embodiments of this aspect have one or more of the following features:

The microscope system is constructed and arranged to record an image area of at least one square centimeter of the surface being examined, the numerical aperture of the lens, its field of view, the scan range and the translation range being cooperatively selected to produce, for a given wave length, at least one million picture elements per $cm^2$ of area scanned.

The wide field of view scanning microscope is constructed to produce images in a transmission or reflection mode, the numerical aperture of the micro objective lens being at least about 0.5.

Preferably the field of view of the micro objective lens is less than about 25 microns, and in many cases is less than about 10 microns.

The wide field of view scanning microscope is constructed to detect fluorescence stimulated by a spot of light passing through the micro objective lens, in which the numerical aperture of the scanning objective lens is greater than 0.6, preferably the field of view of the micro objective lens being less than about 25 microns.

The microscope system is constructed as a transmission microscope, the stationary optics including at least one stationary light source arranged to launch light to the micro objective lens to illuminate a spot on the object being viewed, and a detector system is disposed on the opposite side of the object being viewed.

The microscope system is constructed as a reflectance microscope, the stationary optics including at least one stationary light source arranged to launch light to the micro objective lens to illuminate a spot on the object being viewed, and a detector system is arranged to receive, via the micro objective lens, light reflected from the region being illuminated by the objective lens.

The microscope system is constructed to perform as a fluorescence reader, the stationary optics including at least one stationary light source arranged to launch light to the rotating micro objective lens to illuminate a spot on the object being read with a wave length predetermined to excite a fluorophor possibly present in the object, and a detector is arranged to receive, via the micro objective lens, fluorescing light from the fluorophor at a different wavelength emitted from the region being illuminated by the micro objective lens.

The microscope system is constructed to image detected light upon a pin hole preceding a detector to serve as a confocal microscope. Preferably the objective lens has a numerical aperture greater than 0.6 in this arrangement.

The microscope as a fluorescent reader is constructed and arranged so that the micro objective lens projects, on to the object, an illuminating spot between about 1 to 50 microns in diameter, the micro objective lens having a numerical aperture of about 0.6 or more for collection of relatively low intensity fluorescing radiation.

The scanning microscope has its axis of rotation of the rotary support structure stationary and the translation system for producing relative linear movement comprises a linear stage constructed to move the object to be viewed under the oscillating rotary structure.

The scanning microscope has stationary optics which include a reflector disposed on the axis of rotation of the rotary structure, and a reflector on the rotary structure is disposed on the axis of rotation, the two reflectors arranged in an optical path between the stationary optics and the scanning objective lens throughout the range of rotation of the oscillating rotary structure. Preferably the stationary optics includes a detector to detect light collected by the rotating micro objective lens from the object being scanned.

Preferably stationary optics include at least one stationary light source arranged to launch light to the objective lens to illuminate a spot on the object being viewed.

The scanning microscope system has stationary optics which include a path-deflecting device arranged to vary the portion of the micro objective lens lying in the optical path. In certain preferred embodiments, this feature is combined with a translation system in the manner that the path-deflecting device adjusts the relationship of successive scan paths upon the object being scanned. Preferably in systems in which the object is scanned during both clockwise and counterclockwise rotation of the oscillating rotary support structure, the adjustment made is in the sense of making more uniform, along the length of the scan path, the spacing between the mid lines of the successive scan paths.

The path-deflecting device for a microscope system is a dithered reflector driven in synchronism with the rotary oscillating support structure, preferably this device being a dithered mirror.

The path-deflecting device is an acousto-optical or electro-optical deflector driven in synchronism with the rotary oscillating support structure.

The wide field of view scanning microscope includes a position detector for detecting the position of the oscillating assembly, and including a data collection system that collects data at selected positions determined by the position detector. Preferably a control system for the driver includes a servo control loop that includes the position detector. Also, preferably the position detector is associated directly with the oscillating support structure to determine its position directly; preferably, also, the driver is an electric motor controlled by a servo control loop controlled by the directly determined position of the oscillating rotary support structure.

The wide field of view scanning microscope has the micro objective lens spaced from the center of rotation of the support structure more than 1 cm, the moment of inertia of the rotary structure, excluding the armature of the driver, is of the order of about 25 gm-$cm^2$, for example 30 gm-$cm^2$. Preferably, when combined with a translation system, the frequency of oscillation of the rotary oscillating structure produces in excess of about 10 scan line acquisitions per second. Preferably the radial distance is about 2.5 cm or greater.

The scanning microscope is in the form of a transmission or reflection microscope in which the driver for the rotary oscillating structure oscillates at a frequency of the order of 50 Hz or higher.

The wide field of view scanning microscope has a data collection control system which times the data collection during the scan motion to align data collection points with rows of a predetermined rectilinear raster grid. Preferably the data system converts the data to the raster grid by averaging for each point on the grid, the value of each of two data points in the raster row on either side of the grid point, the values weighted by their respective distances from the grid point in question.

According to another of the contributions, a limited rotation scanning microscope for examination of an object comprises in combination, an aspheric micro objective lens which serves either as the entire objective of the system or as the movable element of a multi element objective lens, having a field of view less than about 20 microns and a numerical aperture greater than about 0.5, a lens-carrying arm mounted and driven to rotate in an arc, in oscillating motion, about an axis that lies normal to the general plane of the object to be examined, the micro objective lens being mounted on the arm at a position spaced from the axis of rotation of the arm so that the micro objective lens is swept in an arc by rotation of the arm, the axis of the micro objective lens being normal to the plane of the surface to be examined, the axis of rotation being stationary, a translating mechanism being arranged to translate the surface to be examined under the rotating micro objective lens, and a light source mounted on a stationary support and associated with optical elements defining an optical path for light to pass from the light source to the micro objective lens, thence to a spot on the surface to be examined.

Preferred embodiments of this aspect have one or more of the following features.

The scanning microscope includes a light source mounted on a stationary support and associated with optical elements defining an optical path for light to pass from the light source to the micro objective lens, thence to a spot on the surface to be examined.

The scanning microscope is in the form of a transmission microscope, light from a spot passes through the micro objective lens and object reaches a detector.

In other forms of the scanning microscope, light from a spot of light passed through the micro objective lens and to the object, returns through the micro objective lens to a detector. In certain cases such a scanning microscope is constructed to read fluorescing light from the object.

The scanning microscope includes a control system for producing coordinated rotation and translation of the object, the microscope constructed to receive data from scan paths generated during clockwise and counterclockwise rotation of the arm, the control system including a compensatory system that varies the relationship between movement of the micro objective lens and translation of the object in a manner tending to make substantially uniform the distance between the mid-lines of the successive scan paths. Preferably, the compensatory system varies the position on the micro objective lens of the light path communicating with the stationary light source, preferably the compensating system comprising a dither mirror.

In any of the microscope systems previously described above that employs a table to receive the object, the table is preferably associated with three adjustable elevators to raise, lower and tilt the table for focusing, and a control system is constructed to conduct a prescan of the object in which data concerning orientation is stored, and a control system responsive to the stored data is effective to actuate the elevators as scanning proceeds to maintain the object in focus.

In microscopes systems previously described above where the micro objective lens is the movable portion of a multi element objective lens and other optical elements are stationary, all optical elements cooperate to perform in a manner similar to a conventional multi element objective lens. The stationary optical elements can cooperate with the movable micro objective lens to optimize energy collection and transfer to the light sensor.

Another contribution comprises, in general, a dither mirror construction comprising a mirror mounted on a flexure and a piezo crystal associated with the mirror in the manner to cause deflection of the mirror on its flexure. This dither mirror is preferably employed in the various scanning microscopes and methods described.

Another contribution comprises, in general, a method of scanning an object in manner to form an image comprising moving in scanning motion a lens of mass less than about 2 gm on a moving structure, directly detecting the position of the lens while collecting light from the object with the lens, and compiling detected data based on positions directly detected at the time of taking the data.

Another contribution comprises, in general, a method of scanning an object employing rotating a lens on an arm in scanning arcs over an object that is translating relative to the axis including deflecting the optical path relative to the lens in a compensatory motion in the sense tending to make substantially uniform the spacing between adjacent scan lines upon an advancing object.

Another contribution comprises, in general, a scanning microscope comprising a micro objective lens mounted to move in scanning motion over an object, stationary optics that produces at least two beams of different wave lengths and a merging system constructed to merge the beams into a single illuminating beam directed to the micro objective lens, the micro objective lens having characteristic chromatic aberration, and a device is included in the path of at least one of the beams to cause rays of one wave length to focus at a point different from the point of focus of another wavelength, the different focusing characteristics of the wavelengths being predetermined in relation to the chromatic characteristic of the micro objective lens to enable focus of the respective wave lengths, by the micro objective lens, upon the object.

In certain preferred embodiments stationary optical elements cooperates with the micro objective lens mounted on the rotatably oscillating arm to form an effective objective of the system.

Another contribution comprises, in general, a rotary scanning system producing arcuate scan motion having a data collection control arranged to time the data collection during the arcuate scan motion to align data collection points with rows of a predetermined raster grid to which the data is to be converted. Preferably, this system includes a data conversion system arranged to convert data to the raster grid by averaging for each raster point the value of each of the two data points in the row on either side of the raster point, the values weighted by their respective distances from the raster point in question.

Other features of the invention will be understood from the following description of preferred embodiments.

DESCRIPTION OF THE FIGURES

FIG. 7 shows how Cartesian data points from the photosensors are arranged in scan arcs and shows the desired uniformly spaced points on a rectilinear raster grid to which the data is to be converted, while

FIGS. 8, 8A and 8B are front, side and top views of one of three similar elevator pin mechanisms that cooperate to focus the microscope slide in the microscope of FIG. 3.

FIG. 9A is a triangular wave representing angular excursion of the rotary structure of FIG. 3 over time, produced by the controls of FIG. 9, while

DESCRIPTION OF PRESENTLY PREFERRED EMBODIMENTS

In the various figures, elements performing similar functions are designated by the same numerals.

Figure 1:
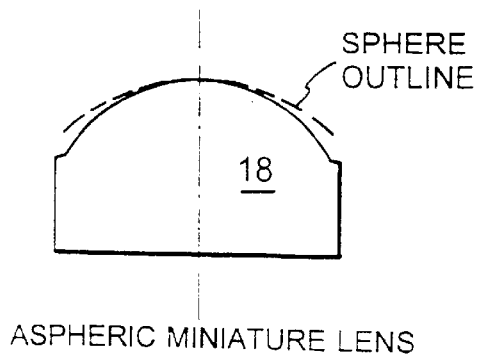
FIG. 1 is a diagrammatic view, on an extremely enlarged scale, of an aspheric micro lens of a type preferred here.

In FIG. 1 is shown, with great magnification, an example of an aspheric micro lens 18 that is useful with the techniques described above. A particular example has a diameter D of 4 mm, a length l of 1.2 mm, a mass of only 0.205 grams and focal length of 2.72 millimeters. This particular lens is one piece of glass. It produces an approximately ½ micron diameter, diffraction limited spot of illumination of all lasers with which it is to be used (e.g., red, blue and green) in conjunction with beam conditioning that corrects for chromatic aberration as described in relation to FIG. 5 below. This particular lens has been selected for transmission microscopy of tissue for telepathology applications, with resolution of 1 micron.

Figure 2:
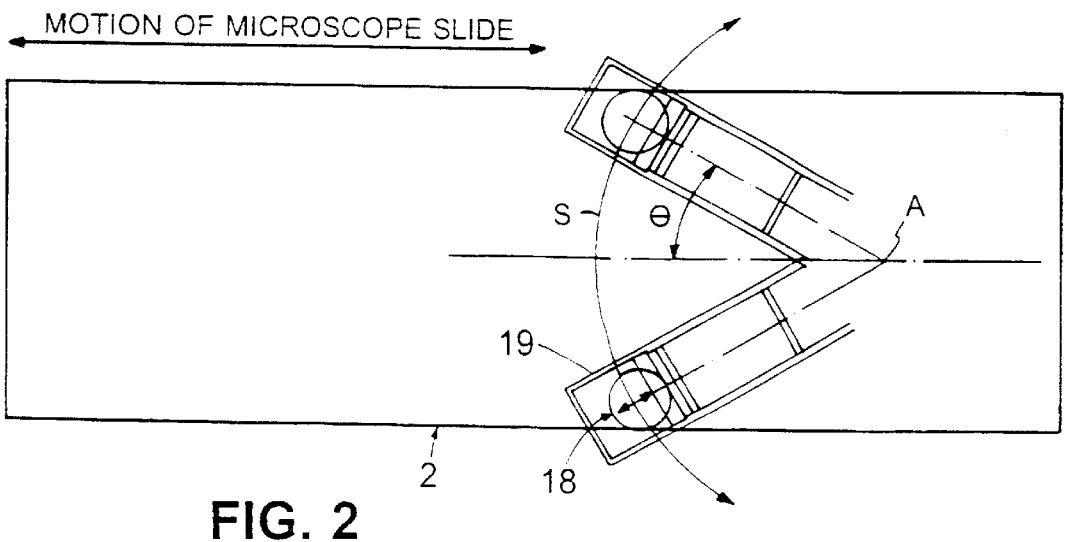
FIG. 2 is a plan view showing the motion of a low moment of inertia limited rotation arm carrying the lens of FIG. 1 in scanning motion and linear motion of a microscope slide beneath it. The motion of the beam upon the lens when employing dither compensation is also indicated.

Referring to FIG. 2, the linear motion of a microscope slide 2 and the limited rotary motion of an oscillating arm 19 carrying lens 18 are depicted. The arm rotates about axis A with an angular range of rotation of the order of 60 degrees.

Figure 3:
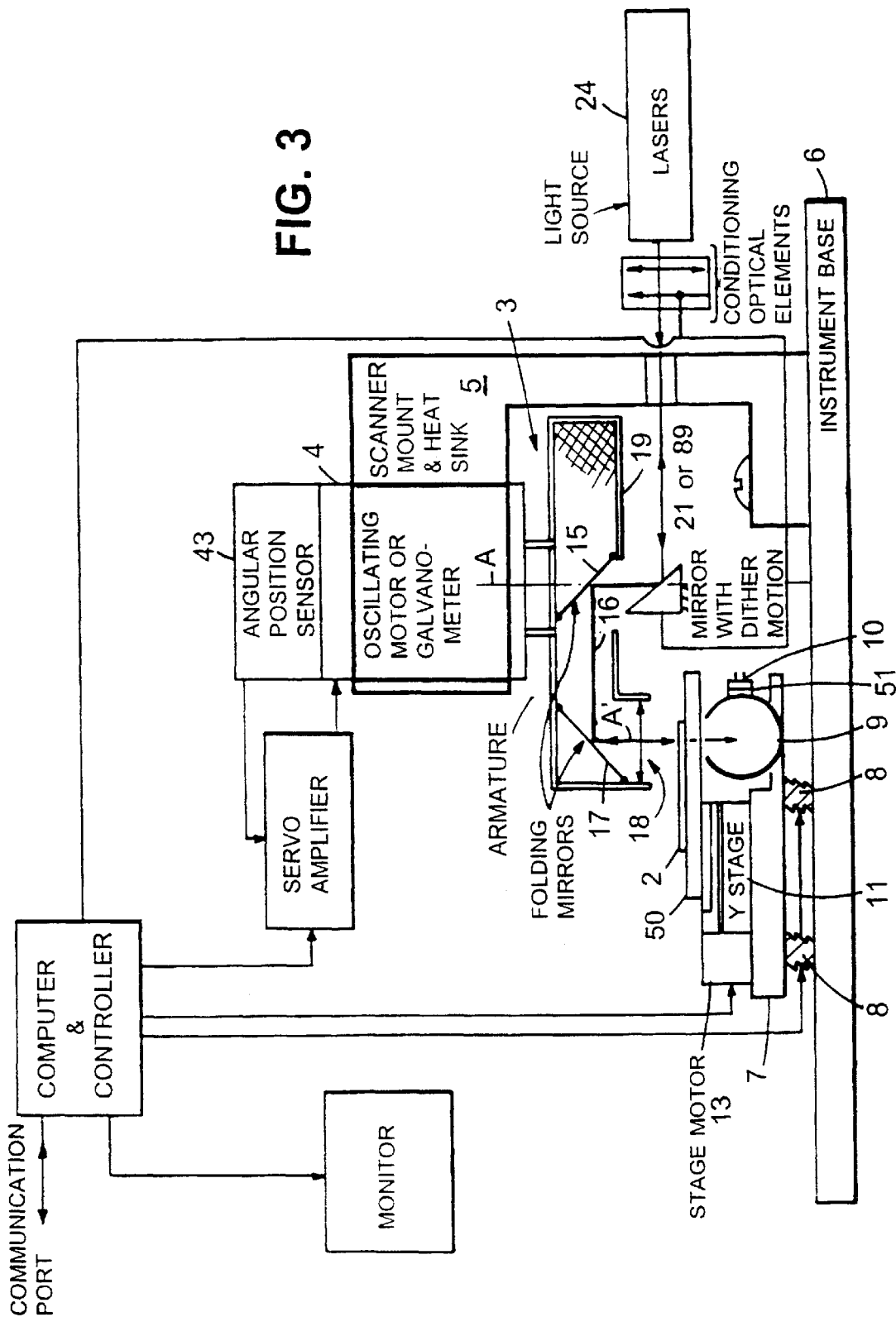
FIG. 3 is a diagrammatic view of a wide field of view, high speed transmission scanning microscope employing rotary oscillation of the micro-objective lens of FIG. 1, using the oscillating arm and the translation movement of an object as depicted in FIG. 2. The oscillating assembly is combined with a position sensor which serves to precisely locate the points of data collection, and functions in a servo-control loop for the driver.

The angular position of the micro objective lens is known from a transducer or sensor associated with the oscillating system. In certain embodiments, an angular position transducer is integral with the limited rotation motor, as shown in FIG. 3. The transducer is shown directly associated with the oscillating arm in FIG. 12 to directly determine instantaneous position.

Figure 10:
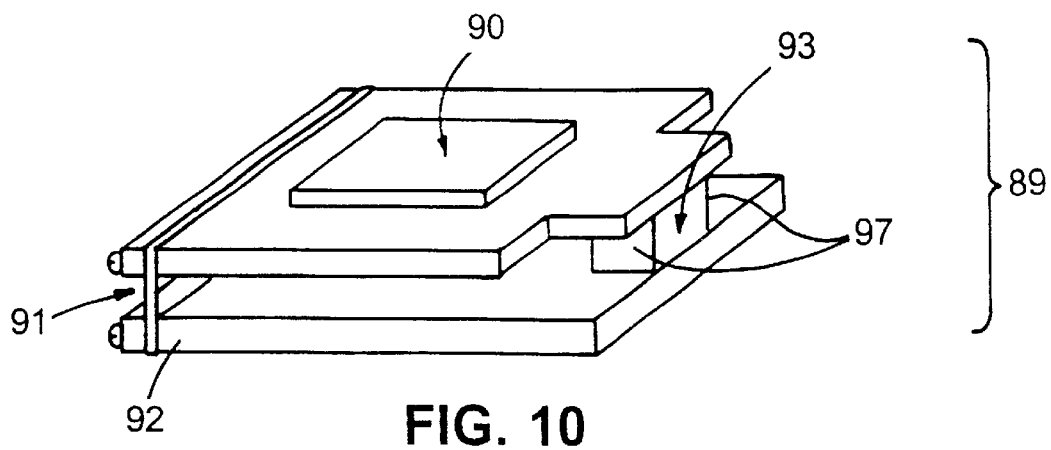
Figure 11:
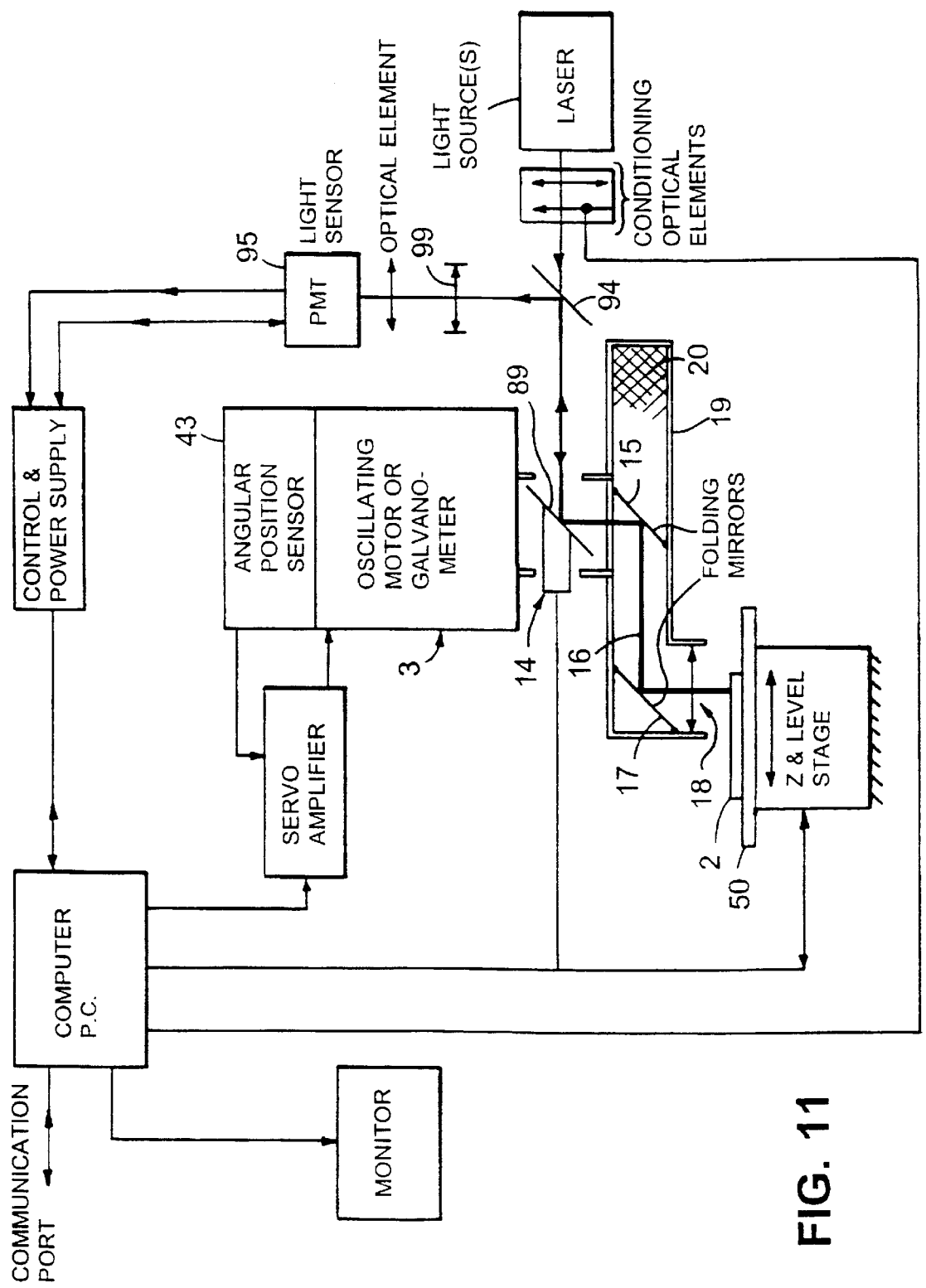
FIG. 11 is a view of a system similar to FIG. 3 showing an alternate periscope construction and dither mirror in the optical path in a reflection microscope.
Figure 12:
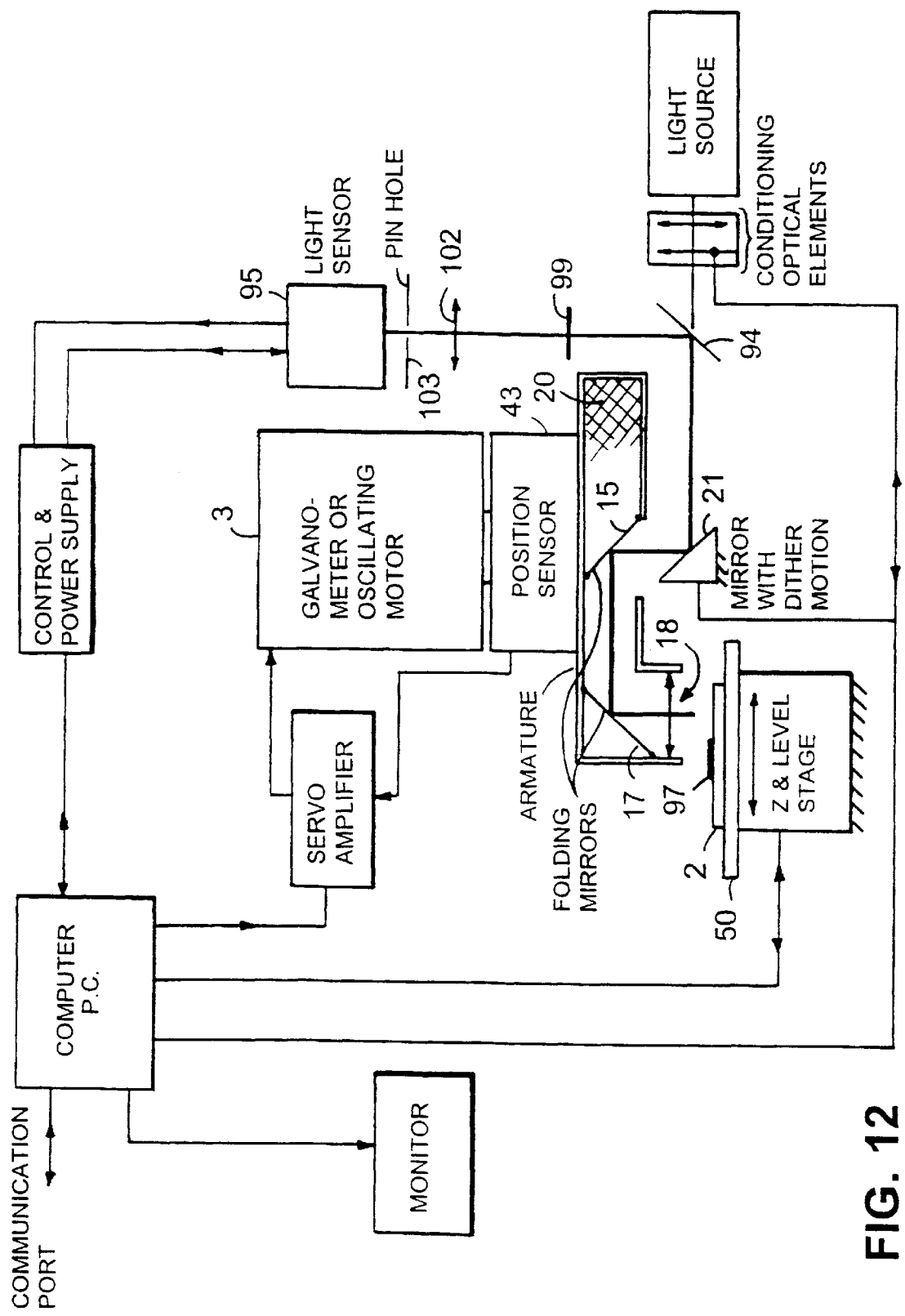
FIG. 12 shows a confocal configuration of a fluorescence reader.

FIGS. 3, 11 and 12 illustrate diagrammatically rotary oscillating structures 19 that carry a micro lens 18. The rotary structure 19 is of extremely low mass and is mounted to rotate on axis A. It carries two turning mirrors, mirror 15 that lies on the axis of the rotating arm and lens-illuminating mirror 17 hat is on-axis with the objective lens 18. Stationary optics include a final stationary mirror 21 that is maintained in alignment with the on-axis mirror 15 that rotates with the scanner arm, to form a periscope. As will be explained in conjunction with FIG. 10 a dither mirror 89 is advantageously substituted for mirror 21 as indicated.

In the embodiments of FIGS. 3, 11, and 12 the object shown to be translated is a microscope slide advanced in the Y direction by a suitable stage 11 while the axis of rotation, A, is stationary. The embodiment of FIG. 3 is a transmission microscope, FIG. 11 a reflection microscope and FIG. 12 a fluorescence reader. All of these embodiments preferably employ aspheric lens constructions and preferably employ a single micro lens as the objective lens.

It will also be understood, however, that depending upon the application, two or more micro lens elements may be combined to form a moving objective lens, paying the penalty of increased moment of inertia.

Figure 13:
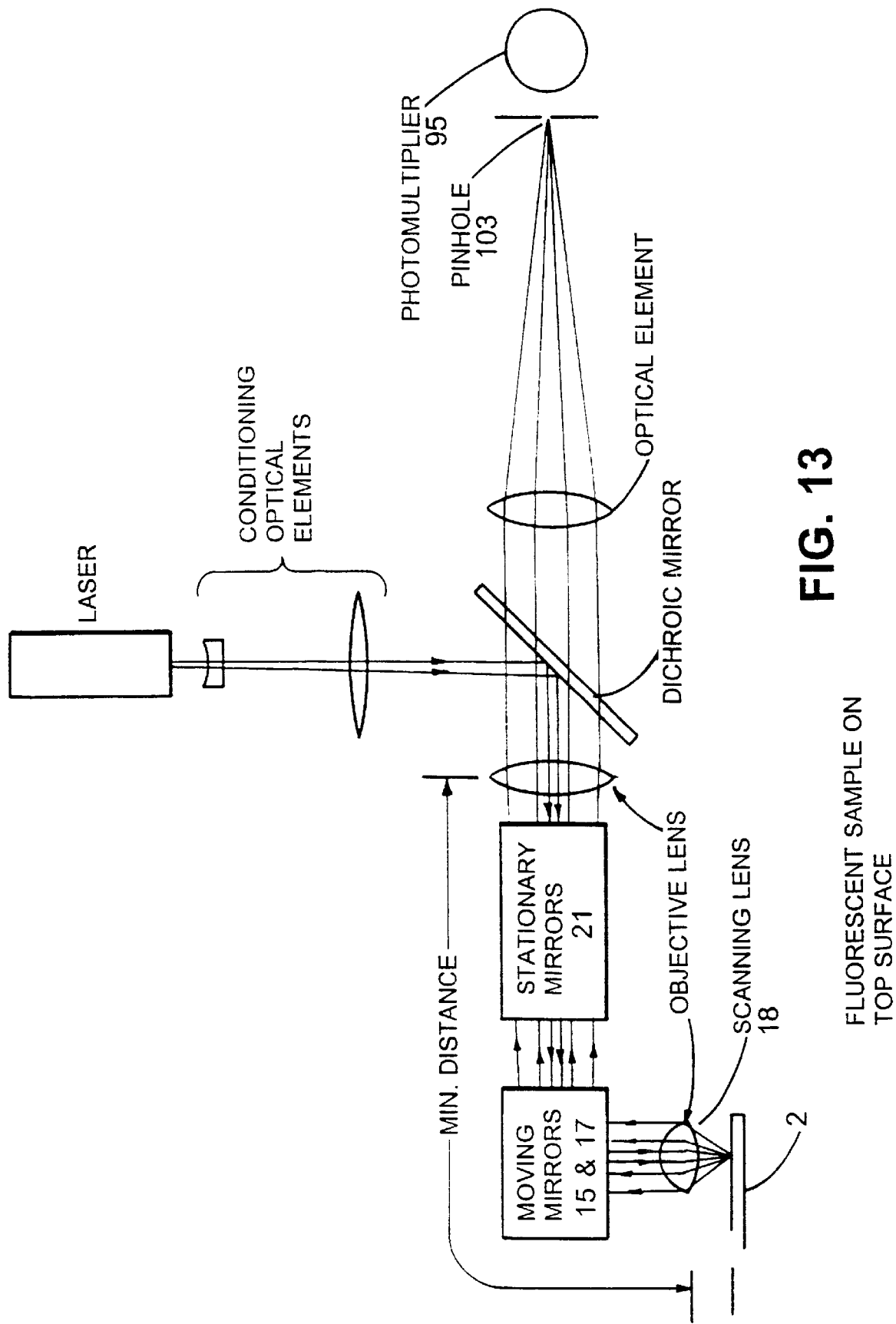
FIG. 13 shows in a symbolic manner a confocal configuration of a fluorescent scanner where the objective lens is comprised of a scanning element and a stationary element.

It will also be understood, however, that depending upon the application, additional lenses or optical elements may be combined to form the objective lens of the system, where one or many such optical elements, preferably a micro lens or lenses, may be installed within the rotating arm. The other optical elements forming the objective may be stationary and in proximity of the moving element. FIG. 13 shows a symbolic construction of this concept in which element 18b is a stationary lens element of the objective.

The transmission microscope of FIG. 3 is suitable for use as a tissue scanner for telepathology. FIG. 3 shows microscope slide 2 to be scanned and an oscillating scanner 3, which includes a limited rotation motor 4. Bracket 5 holds the scanner 3, which in turn is mounted on base plate 6. Both bracket 5 and base plate 6 are of thermo-conductive metal to serve as heat sinks to dissipate the heat generated by the scanner motor 4. Another base plate 7, to accomplish focusing, is moved vertically and tilted by three focus mechanisms 8 at three points in tripod configuration (only two points are shown). On base plate 7 is an integrating sphere 9, which contains three photosensors 10 (only one is shown) to detect light transmitted through the microscope slide 2. Also on base plate 7 is a one-dimensional translation stage 11, which moves microscope slide 2 progressively in the Y direction during scanning.

The photosensors 10 in certain cases have been implemented but in other cases it will be understood that other photosensors may be appropriate to fulfill the requirements of the particular task. For example, photomultiplier tubes, pin diodes, avalanche photodiodes and other photosensors may be employed.

Extending between microscope slide 2 and oscillating arm 19, is the light path arm 14. It delivers laser light from stationary laser 24 to the center of rotation of the oscillating arm 19, terminating with mirror 21 that directs the beam axially upward toward mirror 15 on axis A that rotates with arm 19. The laser light, after traveling upward along axis A, is reflected by mirror 15 radially outward along the oscillating arm 19 in horizontal path 16. At the outer end of arm 19, the light is reflected at mirror 17 to travel vertically downward through objective lens 18 along axis A' which is parallel to rotation axis A, perpendicular to the plane of rotation of arm 19 over the object. The light passes through the microscope slide 2, and that light which is not absorbed enters integrating sphere 9.

The oscillating assembly is characterized by a very low moment of inertia, less than 50 gm-cm$^2$, preferably of the order of 25 gm-cm$^2$, and about 10 gm-cm$^2$ in the preferred embodiment, and has a mass of less than 25 grams. The moment of inertia and mass refer to the oscillating structure of the arm 19, the mirrors 15 and 17 that it carries and the objective lens 18, and does not include the moment of inertia of the rotor of the limited rotation motor itself. In most cases, highest performance can be got when the moment of inertia of the rotor of the limited rotation motor is approximately the same as that of the load being oscillated, and the rotor is chosen to have a moment of inertia generally close to 10 gm-cm$^2$, although rotors having moments of inertia between about 5 and 30 gm-cm$^2$ or even more will perform adequately in many cases.

Lowest inertia of the oscillating assembly, in the presently preferred embodiment, is made possible largely by the micro lens 18 being a single small element weighing on the order of two-tenths of a gram. The distance from the axis of rotation A of arm 19 to lens 18 in this embodiment is about 25 millimeters. The arm is made of half millimeter thick sections of aluminum that serve to minimize its mass.

While for tissue scanning application lens 18 may have a numerical aperture between 0.5 and 0.6, higher numerical apertures, readily achieved by the unique scanning micro lens objective, are very important when the microscope has other uses. For instance when larger spots are used, with small diameter laser beams as input to the lens, a low mass, high numerical aperture micro lens of numerical aperture greater than 0.6 is especially efficient at collecting fluorescent light emitted from samples and sending this light back along the original direction of the incident laser beam to a beam splitter. This will be described later, in connection with FIG. 12.

Likewise, to achieve high numerical aperture, the composite objective, formed by a moving micro objective lens and the stationary elements, as symbolized by stationary lens element 18b in FIG. 13, can be employed.

Figure 4A:
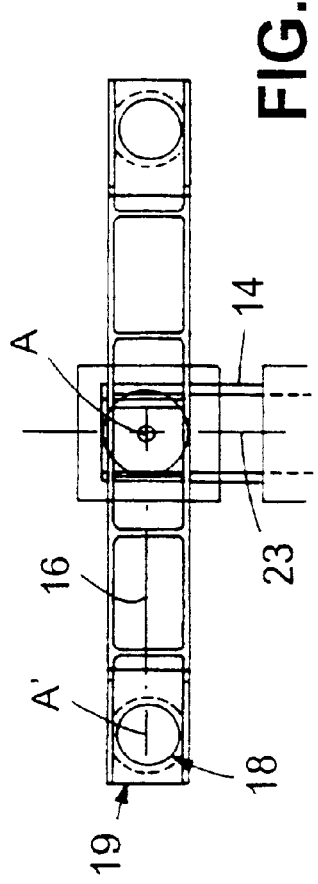
FIG. 4A is a top view of the arm, lens and mirrors.
Figure 4:
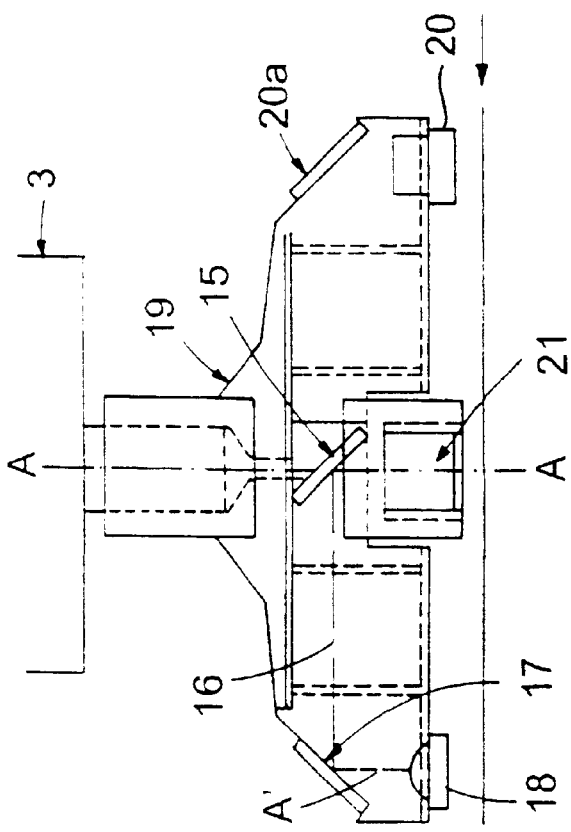
FIG. 4 is a highly magnified elevation of a portion of FIG. 3, showing the side of scanner arm which carries the aspheric micro lens and mirrors that deliver light to the lens.

FIG. 4, a magnified view of portions of FIG. 3, shows primarily the oscillating arm assembly. In a symmetrical construction counterweight 20 has approximately the same mass as the aspheric micro lens 18, and counterweight 20a has the same mass as mirror 17, both counterweights being disposed the same distance on the opposite side of the axis of rotation A from the elements 17 and 18 that they counter balance. Nn non-symmetrical constructions, the masses of the counter weights may be different, with different distances, selected to achieve the counterbalanced condition, or other balancing techniques may be employed.

As shown in FIGS. 4A and 4C, the stationary arm 14, extending over microscope slide 2, delivers light to the stationary mirror 21 at the center of rotation A of the oscillating arm. The light is reflected upwards along axis of rotation A to mirror 15 on the rotating assembly. The light proceeds radially along path 16 to mirror 17 which direct the beam down along axis A' to the micro lens 18. The top view FIG. 4A shows the micro lens 18 in plan.

Figure 4B:
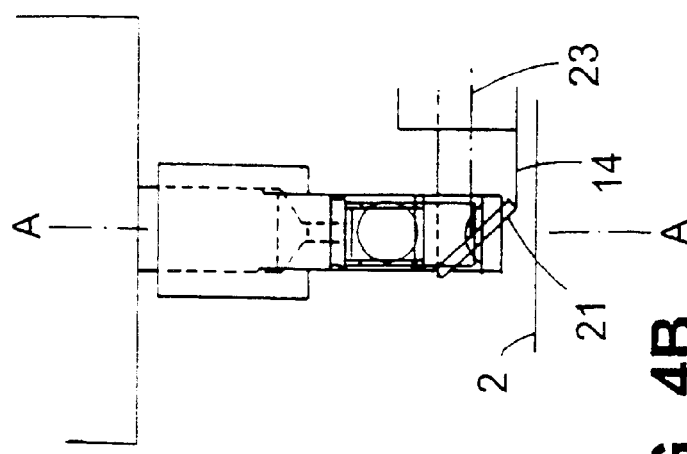
FIG. 4B shows an end view of this arm and the mirror which delivers light to the arm.

For completeness, referring further to FIGS. 4A and 4B, the light path 23, prior to being reflected by mirror 21, is horizontal in the stationary, cantilevered optical arm 14 and is nearly at a right angle to path 16.

It will thus be seen that the length of the light path from laser 24 to lens 18 is constant throughout the scanning range. This enables the use of simple alignment techniques.

Referring further to FIG. 3, after transmission of light from the micro-lens through the microscope slide, there are three photosensors 10 that collect the different colors of light in integrated sphere 9. In front of each photosensor 10 is filter 51 to ensure only the desired wavelength reaches the respective photosensor 10.

Arm 19 and its assembly can be driven with an optical scanner motor such as model M3 from General Scanning, Inc. or model 6880 from Cambridge Technology Inc. It can also be driven with a moving coil motor that is similar to that used in rotating disk memory systems.

Turning briefly to FIG. 12, a simplified modification of the drive system of FIG. 3 is shown in which the prime mover is a conventionally rotating DC electric motor such as a Portescap brand moving magnet stepping motor, for instance model 26 BC-4C-101. The low torque requirements of the system permit the use of such inexpensive motors. While, for simplicity, an inexpensive electric motor is employed, in other embodiments a torque motor such as manufactured by Aeroflex or SL-MTI, a galvanometer, or a resonant structure may be employed. In all of these cases, position information for the data collection system and servo control is derived from the instantaneous position of the rotary assembly. As depicted in FIG. 12, the transducer is secured directly to the rotating arm 19, so that even any variations due to bearings or compliance of the shaft do not affect the accuracy of the position information.

Chromatic Aberration Compensation

Figure 5:
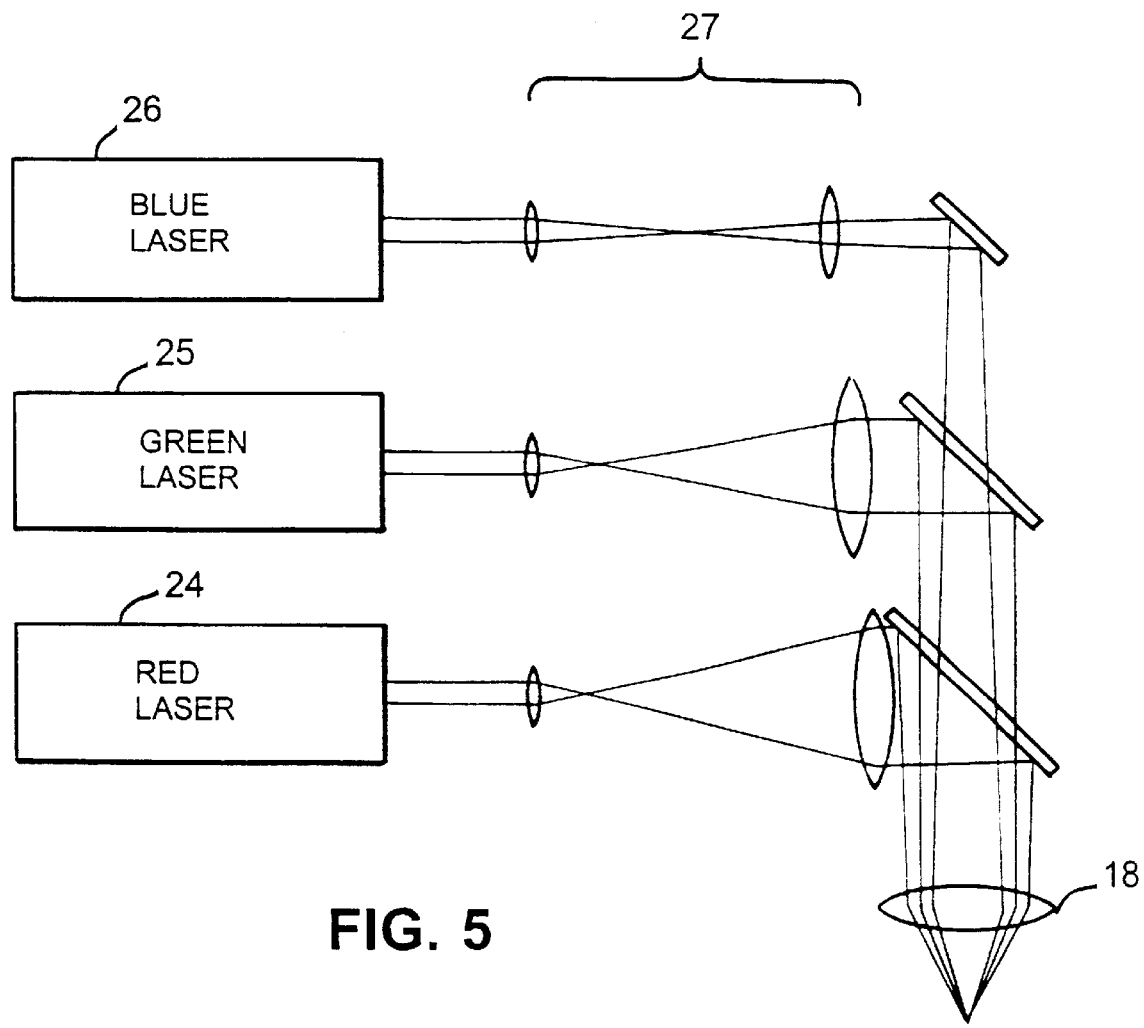
FIG. 5 shows three lasers that supply light to the oscillating arm of the system of FIG. 3, and shows how the light beams from the lasers are combined to compensate for conditions in which the micro lens has a different focal length for each of the three laser wavelengths.

Referring to the schematic representation of FIG. 5, a red emitting laser 24, a green emitting laser 25 and a blue emitting laser 26 are each associated with a respective adjustable beam expander 27 made in the customary way of 2 lenses. All of these are part of the stationary optical assembly.

The micro objective lens 18, which in preferred embodiments is an aspheric lens, may have different focal lengths for each of the 3 laser wavelengths involved. Referring to the schematic FIG. 5, for all wavelengths to focus at the same height on the microscope slide, the red laser beam is made to converge as it approaches micro lens 18, the green beam is perfectly collimated, and the blue beam is made to be diverging as it approaches the micro lens. This is accomplished by corresponding defocusing of the red and blue beam expanders 27 of FIG. 5. As a result of the differing effects of the single objective lens 18 upon the light of differing colors, light rays of all colors come to focus at the same height on the object being scanned.

Other techniques to implement compensating defocusing to counter-act opposite defocusing qualities of the micro lens 18 can be employed. For example a composite conditioning lens of two or more glasses can transform a collimated chromatic beam to defocus respective wave lengths for incidence upon a micro lens that has opposite chromatic aberration. Some of these lenses could be stationary lens 18b shown in FIG. 13.

Data Transformation

FIGS. 2, 6, 7 and 7A illustrate the arcuate scan traces S on the microscope slide. For purposes of description the case depicted is that the microscope slide is stationary during each scan. (In certain preferred cases the slide moves continuously, but the principle to be illustrated will remain the same.)

Figure 7:
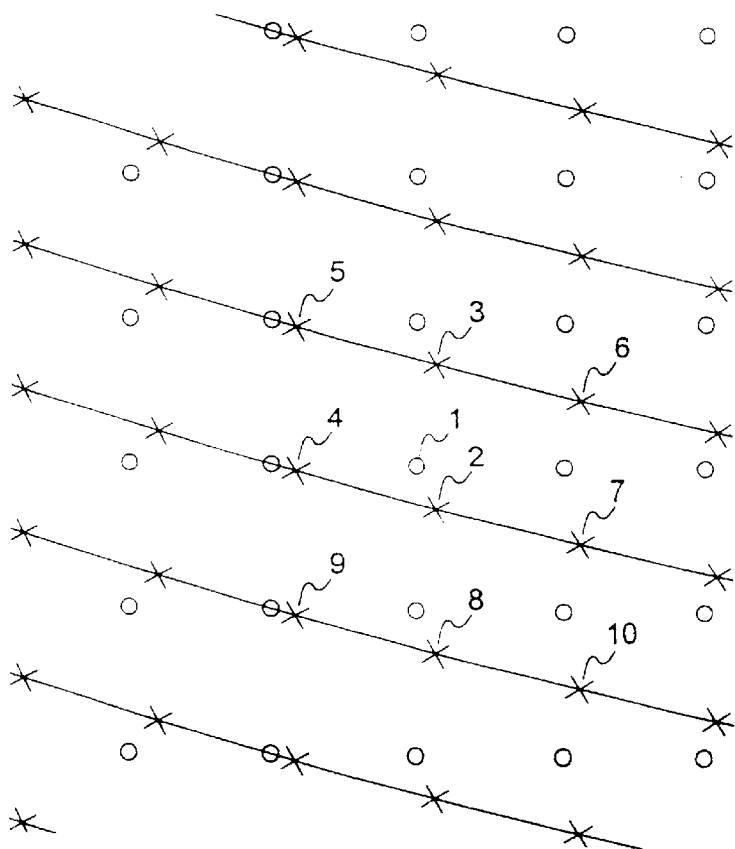
Figure 7A:
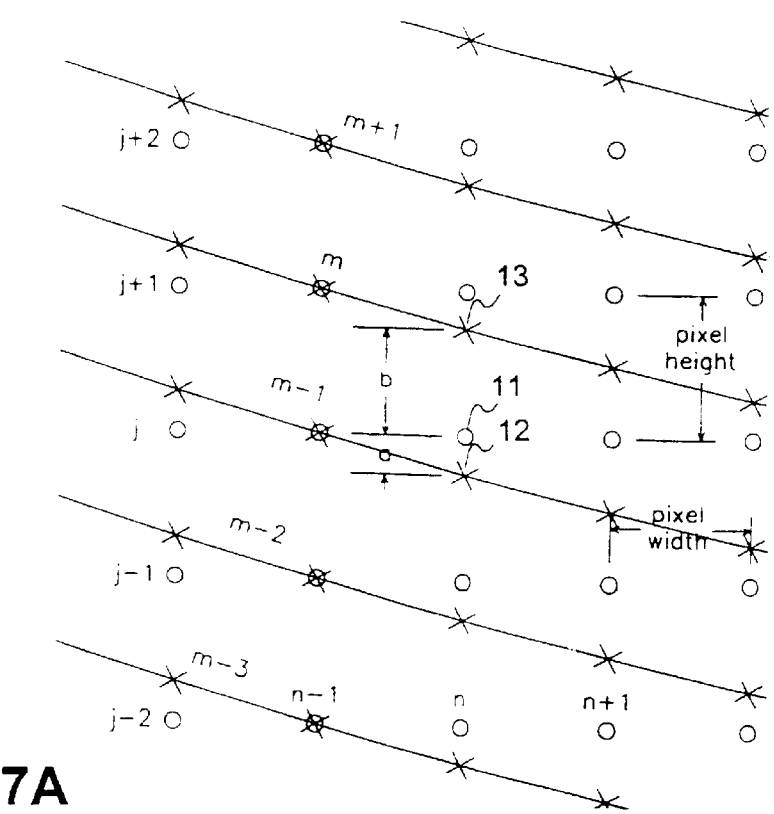
FIG. 7A shows an alternative data collection scheme for use with a special high speed interpolation algorithm by which data values are interpolated to establish the data in raster format.

The measurements made by a photosensor detector associated with systems of FIG. 3, 11 and 12 are illustrated with crosses in the magnified views of FIGS. 7 and 7A.

Figure 6:
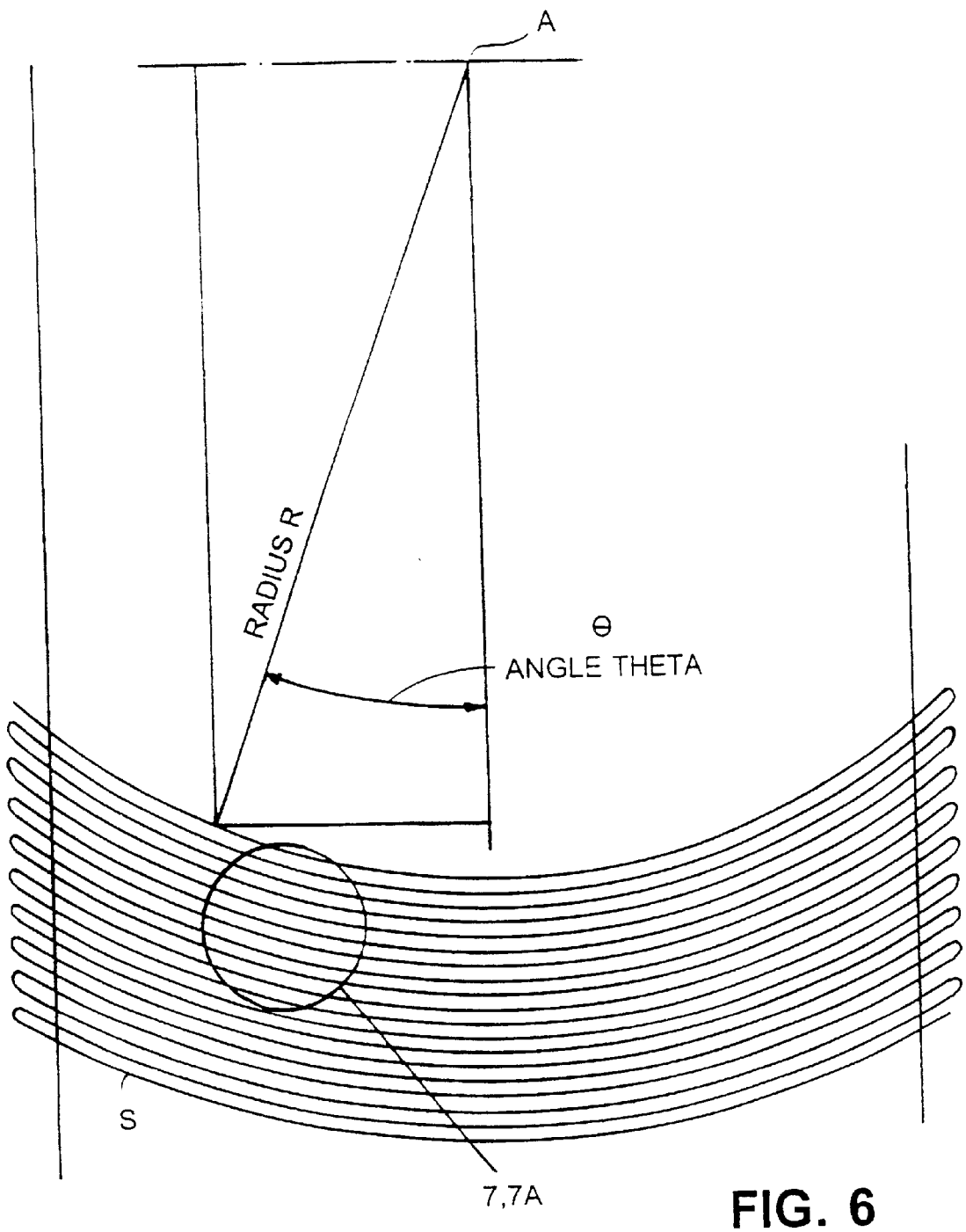
FIG. 6 shows data points taken at uniform arc increments during successive scans by the systems of FIG. 3 in the case of step motion of the object.

The software of the system keeps track of the angular position of the objective lens and, employing with reference to FIGS. 2 and 6, the relationship:

$Yi = Y + CBR(1 - \cos \theta)$ $Xi = R \sin \theta$ the system assigns detected values to each point of resolution, converted from polar to Cartesian coordinates.

Thus, the crosses of FIGS. 7 and 7A show the location of each data point actually measured by a photosensor. The O's in FIG. 7 and 7A show the equally spaced locations on a rectilinear grid in raster format for producing images on conventional monitors and for data transmission. All commonly available image display devices, e.g. high resolution TV monitors, have rectilinear arrays of sites at which light is emitted. These devices can be employed with the microscopes of FIGS. 3, 11 and 12 by the conversion of the input data to correspond to a rectilinear raster array rather than to a series of arcs.

For this purpose an interpolation algorithm calculates the transmission values for the O's using transmission values that correspond to nearby crosses for each point O.

Preferred implementations for the systems of FIGS. 3, 11 and 12 may employ a limited rotation driver that is caused to scan successive arcs across the microscope slide at constant angular rate. As it scans, an analog to digital converter digitizes the intensity values of light received from the microscope slide.

A way to transform the data to raster format is explained by reference to the locations numbered 1 through 10 in FIG. 7. The result of the transformation will include a transmission value for the location at point O numbered 1, for example. This value will be a weighted average of the measured values at nearby locations such as locations 2 through 10.

The literature describes many operable methods to do this, involving Fourier transforms, wavelet transforms, etc. A simple method is a weighted average of the transmission values at four locations 2 through 5, with the weighing factors decreasing, the greater distance the data point is from the raster point for which value is being interpolated. This method involves looking up previously stored weighting factors based upon the distance from location 1 to each of the four original data locations, performing four multiplications and summing the four resulting products. The weighing factors can be pre-calculated and accessible from a store since it is known in advance, from the sampling controls, where all of the O's and crosses are located.

Where it is desired to operate extremely fast, as in telepathology, the time required for four multiplications can be a problem with the present state of low cost computers because it is desirable, for instance, to transform data for one O approximately once every 175 nanoseconds. (At this rate the process of transforming the data can keep up with the process of taking data with the system that has been described.)

A further contribution presented here is a technique to reduce the job from four multiplications to one or two by taking data, not at uniform intervals along the scan trace S, but in the same uniform intervals in the X coordinate that describe the locations of the O points in the desired rectangular raster pattern. FIG. 7A shows that, in this case, the transmission value for location 11 can be just a weighted average of the. transmissions at locations 12 and 13. If the measured transmission at location 12 is r(m−1,n), the measured transmission at location 13 is f(j,n)=(b×r(m−1, n)+a× r(m, n))/(a+b). The letter r stands for raw data, the letter m numbers the arc-shaped scan lines, the letter j numbers the rectilinear horizontal rows, and the letter n numbers the columns that extend in the direction of motion of the microscope slide. In this manner rapid interpolation to raster format is made in a simple way.

While the system has been explained with reference to scanning at constant rate of rotation, scan rates that vary in a predictable manner may be employed. The same principles as described are useful, with the control system being suitably adapted still to take the samples at the crossing points of the raster grid.

Adjustment of Focus

As the location of the surfaces of objects to be examined may vary with respect to the focal plane, precise adjustment of focus can be important to realize high speed, wide field, high resolution microscopy. For example, the ISO 8037-1- 1986E industrial standard for microscope slides specifies the tolerance of their thickness to be 300 micrometers. This is approximately two orders of magnitude greater than the depth of field of the one micron resolution microscope described in FIG. 3. The top surface of a slide may tilt in one or another direction. Also the slide may be bowed in its lengthwise direction. The microscopes being described advantageously include a dynamic focus capability that employs controllable elevator focus mechanisms. One of three focus mechanisms 8 employed in the embodiments of FIGS. 3, 11 and 12 is shown in FIGS. 8 and 8A and 8B. Focus mechanisms 8 move base plate 7 vertically. The presence of three of these mechanisms, spaced in a triangle, enables plate 7 to be lifted, lowered, or tilted for focusing. Each mechanism 8 is driven by a linear actuator 143 which advances a shaft 44. The actuator internally is similar to a stepper motor with 96 steps per revolution. The shaft 44 drives the long arm of a lever 45 which accomplishes a reduction of a factor of 20 in the motion of the shaft, i.e., for every ⅛ mil step of the linear actuator 143, the base plate 7 moves only ¹⁄₁₆₀ of one thousandth of an inch.

The lever 45 pivots about pivot point 46. The pivot and connection to both ends of the lever are provided with three flexure springs 47. The flexure springs 47 are kept always in tension by bellville spring washers 48 to minimize backlash in the linear actuator 143. The base plate 7 is restrained to move only vertically relative to the machine base plate 6, and not laterally, by three thick flexures 49, one associated with each focus mechanism 8.

The components that move vertically in response to actuation of the focus mechanisms 8 move the microscope slide 2. Plate 50 which holds the microscope slide 2 connects the microscope slide with the linear stage 11 that is carried by base plate 7.

In the case of the transmission microscope of FIG. 3, the integrating sphere 9 is also moved vertically, and so moves with the microscope slide. In this embodiment, the oscillating arm 19 and motor 4 do not move relative to the machine base plate 6.

Thus, the microscope slide is moveable under computer control in a number of degrees of freedom to place the point on the sample under investigation in the focal plane of the scanning microscope. There may be no need to compensate for yaw during scanning movement in the embodiments shown, since the narrowest dimension of the microscope slide is relatively rigid and uniform.

In the embodiments shown, the focus correction is detected by photosensors 10 detecting modulation of the light by the tissue sample or by fiducial points. As the tissue sample approaches perfect focus, the amplitude of the high frequency components in the signal of the photosensors is increased relative to that of the lower frequency components and best focus is defined as that height of the microscope slide at which the ratio of high frequency components to low frequency components is maximized.

Prescan of the microscope slide enables determination of the height of best focus of the microscope slide at a chosen grid of points on the microscope slide. This enables detection of whether the slide is tilted or bowed. This information is stored in computer memory and accessed during the progress of the subsequent fine resolution "examination" scan.

During the examination scan the microscope slide is held on its support in exactly the same position it occupied in the prescan. When the examination scan occurs, the focus mechanism continually tracks the surface of the microscope slide in accordance with the stored data.

For conducting the prescan, the positions of the adjusting mechanisms are dithered and a suitable computer program analyzes the data from successive measurements made by the photosensors to find to what extent the flow of data contains high, medium or low frequency components.

In regard to gross height error due to pitch, roll or bow the computer program analyzes the prescan data and determines gross tilt correction. The actuators are accordingly set to correct gross tilt prior to the examination scan.

Thereafter, in the embodiments described, it is preferred that some adjustments be made dynamically and some not. In this discussion, roll is rotation about the long axis y of the microscope slide, the direction in which it advances, and pitch is rotation about the short axis of the slide. During the examination scan, as the linear stage 11 moves gradually while the microscope slide is scanned repeatedly, the position of the microscope slide is continually adjusted by focus mechanisms 8 based upon the stored prescan data for pitch and bow.

In other preferred embodiments, auto focus techniques as described in U.S. patent application Ser. No. 09/079,790, filed May 15, 1998, are employed. The disclosure of that application is hereby incorporated by reference.

Control System

Figure 9:
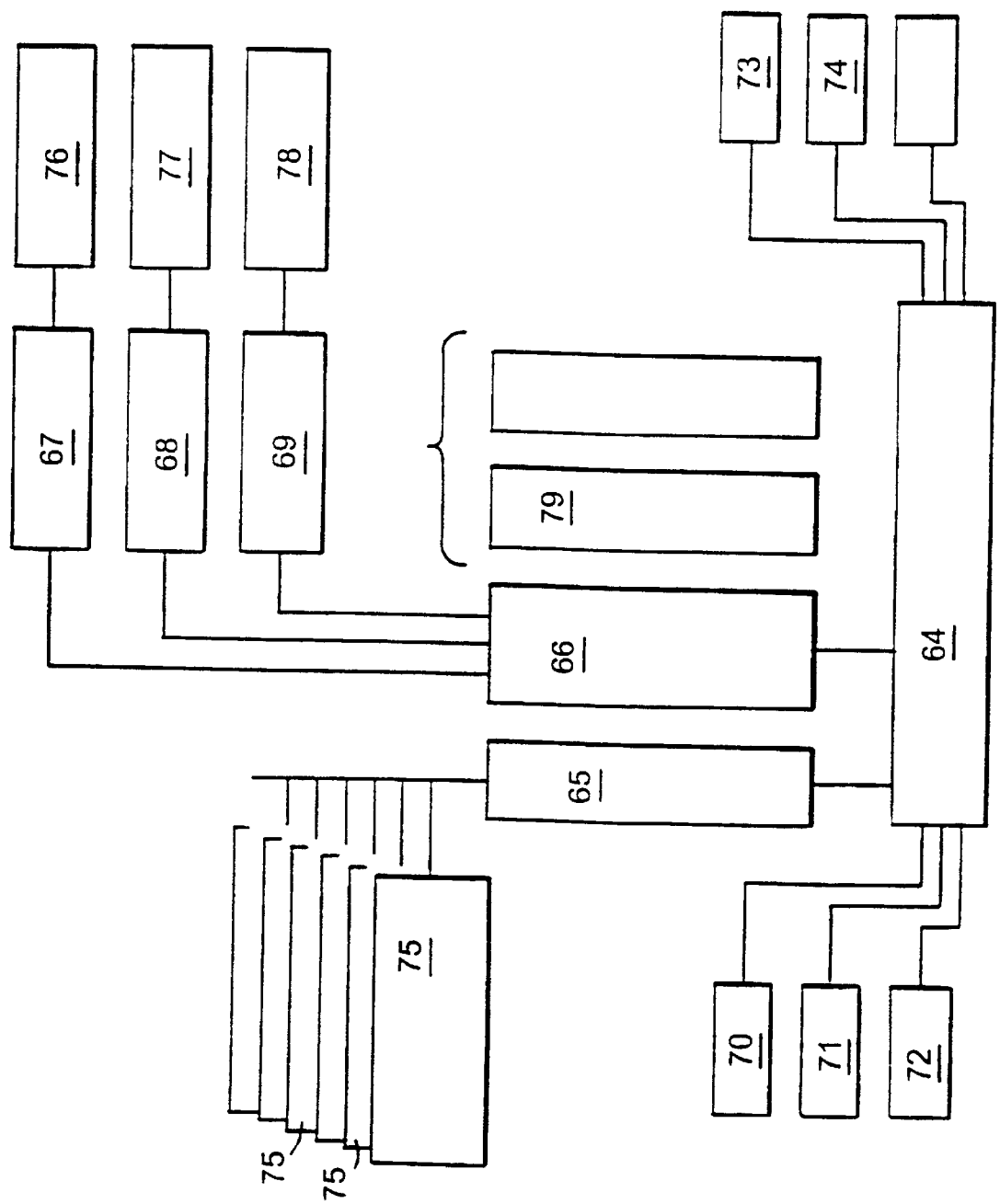
FIG. 9 is an electrical block diagram of the system used for collecting and processing signals.

FIG. 9 is an overall electrical block diagram of the control system for the microscope of FIG. 3. (With minor changes as will be obvious from the further discussion, the same system is useful for the embodiments of FIGS. 11 and 12).

Motherboard 64 of a personal computer 60 holds a digital signal processor board 65 which processes the signal from the photosensors and a real time control computer board 66 which controls the galvanometer or other driver, the stepper motors and other sensors and actuators within the system. The electronics 67, 76 for driving the limited rotation motor 4, the electronics 68, 77 for driving the stepper motor 13 and the linear actuator 93 are also shown, as are electronics 69, 78 for miscellaneous functions. The personal computer mother board 64 also contains circuitry and connections for supporting standard computer peripherals, namely a monitor 70, a keyboard 71, a mouse 72, a hard disk 73, and a floppy disk 74. Also shown are six photosensor amplifier circuits 75 for the three colors of light, both as sampled directly from the emitting lasers, and as detected following exposure to the object being examined. Block 67 generates a triangular wave for driving the limited rotation motor. Its signal goes to a servo control board 76 which applies power to the limited rotation motor and processes the feedback signal from the angular position transducer. The controller for the stepper motor 143 and the linear actuators 43 referred to as block 68 feeds low level signals to a power amplifier board 77 which provides the power signals for driving these various motors and actuators. Similarly, the miscellaneous block 69 provides low level signals to a higher power board 78. Spare slots are provided for additional capabilities such as an Ether Net communication link.

Operation of Transmission Microscope

A typical operation of the presently preferred embodiment of the tissue scanning transmission microscope of FIGS. 3–9 will now be described.

A slice of tissue is placed on the microscope slide 2 in a conventional way. The user places the microscope slide in slide holder (not shown). By pressing a button, the machine automatically moves the slide inwardly toward the oscillating rotary arm 19. First the slide is prescanned. As the slide passes under the oscillating arm 19, not only will it be moved linearly by stepper motor 13, but the focus actuators 8 are moved vertically in a dithering action to find the height of the slide which gives the best focus at respective points across the slide. While this is happening, the photosensors send their signals to the electronics described in FIG. 9, and the computer program causes examination of the output. For each height of the microscope slide, the software calculates basically the magnitude of the changes in transmitted light from one sample to the next. When these changes are at their maximum the slide will be at its best focus, and this data is recorded.

The raw data points are placed in memory at a very high rate and the software accesses them at a lower rate or, in some cases, takes periodic samples. The prescan transmission through the slide is displayed on the monitor for the operator and the portions of the microscope slide which contain interesting material, mainly absorbing material, are shown on the monitor. The operator is enabled by the controls to specify parts of what he sees for examination. After the fast pre-scan has been performed, the best focus found from the acquired data, and a relatively crude version of the image, based on prescan data, has been displayed to the operator, the operator selects the portions of the image to be scanned. In response, the microscope slide moves fast to present the selected region, and then moves slowly forward for microscopic examination of the slide by a fine scan motion. This is done with an increment of advance of only about $3.5/10$ of a micron per scan of the oscillating arm, which provides about 30% overlap between adjacent ½ micron diameter spots. It should be noted that a 1 micron resolution requires ½ micron pixalation in order to address uncertainties defined by the Nyquist criterium. The oscillating arm oscillates at 50 cycles per second in a triangular wave pattern, providing 100 scans per second, the slide moving $3.5/10$ of a micron per scan, so that the slide moves at the rate of 35 microns per second. To examine 1 cm length of slide it takes less than 5 minutes under these conditions. After the desired scanning is complete, the slide returns to the original position for removal.

The data collected during the fine scan (the detected laser light divided by a value representing the incident laser light for each resolution point) has the arcuate nature of the data collection points eliminated by interpolation to raster format. Then the data is put on a hard disk or read-write magneto optic disk, or sent over a wide band-width communication link which may be a satellite link to a physician on the other side of the. world, or by data line to another location in the same hospital or facility, or to a patient's permanent medical record.

The electronics of FIG. 9, in the preferred embodiment, drive the limited excursion motor 4 at constant angular velocity during the data taking part of excursions. Scanned data may be taken in various ways, for instance, with index motion of the object between scans, taking of data with clockwise rotation only or with both clockwise and counterclockwise motions of the limited rotation assembly. FIG. 9A, a triangular wave form illustrates constant angular deflection of the assembly during both clockwise and counterclockwise excursions for data acquisition.

Scan Motion Correction

For achieving fast, accurate scanning, it is preferred to advance the object at constant velocity, while taking scan data with both clockwise (cw) and counterclockwise (ccw) rotations.

Figure 9B:
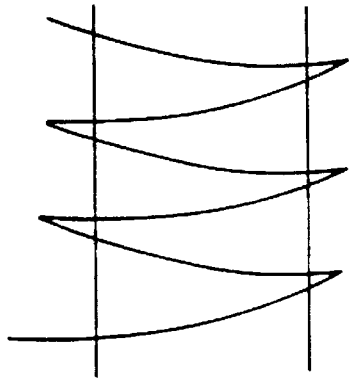
FIG. 9B illustrates the shape of the scans upon a continuously moving object, using the scan rate of FIG. 9A, in the absence of a dither mirror.

With the light path to lens 18 fixed and the microscope slide advancing at a fixed rate, the scans across the microscope object in cw and ccw motions form a generally curved triangular pattern on the slide, as a result of the combined rotational oscillation motion and continual linear translation, FIG. 9B. The spacing between adjacent scan paths is not uniform along the scan arcs. This leads to inefficiencies, related to the need for significant overlap of scans in some regions in order to at least cover the surface of the objective in other regions.

Another contribution presented here is a motion compensating action that improves scan efficiency for this case.

Figure 10B:
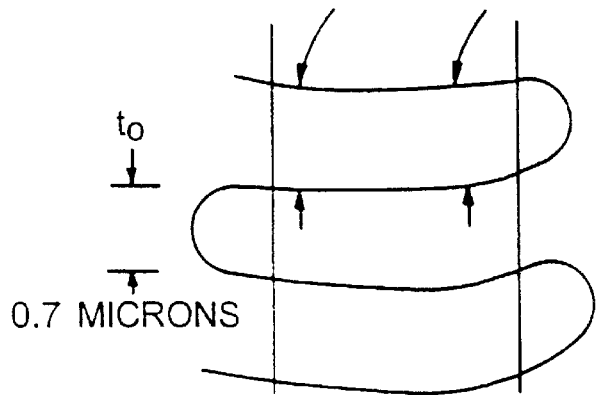
FIG. 10 is a magnified perspective of a dithering mirror.
FIG. 10A is a wave form of angular excursion of the dither mirror, on the same time base as FIG. 9A, for producing compensating movement of the beam, while FIG. 10B, similar to FIG. 9B, shows how the dither mirror of FIG. 10 produces more uniformly spaced arcuate scans upon the continuously moving object.

In this embodiment the compensation system is arranged to shift the light path relative to the rotating lens, in the radial direction of the supporting arm 19 (see FIG. 2) in coordination with the rotary oscillation in accordance with the deflection pattern shown in FIG. 10A. This causes the successive scan paths to be more closely parallel, as shown in FIG. 10B.

From inspection of FIGS. 9A and 10A it can be seen that as the scan arm changes direction at the end of its trajectory, and traces an apex, the beam is retarded with respect to the linear motion of the target, and when the objective re-enters the scan area, the beam is accelerated. This is achieved when the dither mirror follows a motion defined by FIG. 10A while the scan arm with the objective, is driven as indicated on FIG. 9A. Also, during the scan itself, further deflection of the mirror compensates for the trigonometric function related to the angle of deflection of arm 19.

In the presently preferred case, dither mirror 89, FIG. 10, is added to the transmission microscope system of FIG. 3 in place of mirror 21. (A reflective microscope system also employing the dither mirror 89 in place of mirror 21 is shown in FIG. 11 and a fluorescence reader employing dither mirror 89 is shown in FIG. 12).

The nonuniformity of scan spacing is improved upon considerably by moving the reflecting surface of dither mirror 89 through a very small angle, for example, approximately $10^{-4}$ radians.

As shown in FIG. 10 the preferred dither mirror 89 comprises a small mirror 90, approximately 1 cm$^2$ in area and about 1 mm thick. One edge of the mirror is connected with a fixed supporting structure 92 by a flexure 91, forming a hinge. At the other end of the mirror is a piezoelectric actuator 93 such as the Nippon Electrical Company AE0203D08, a small inexpensive actuator which has a 10 micron range of motion when 100 volts are applied to leads 97 to introduce controlled current to the piezo crystal actuator 93. Since, for example, the spacing between adjacent scans may be $3.5/10$ of a micron on the microscope slide, the dither mirror is provided with a range as measured at the microscope slide of about $3.5/10$ of a micron to make more nearly uniform the spacing between the scans. The angular rotation required of the laser beam itself to achieve this is $3.5/10$ of a micron divided by the focal length of the micro lens which in the example is 1.2 mm, resulting in about $1 \times 10^{-4}$ angular range of the laser beam. The mirror rotates only half of that or about $4/10 \times 10^{-4}$ radians. The voltage to accomplish that is of the order of 10 volts applied to the piezo-electrical actuator. The resonant frequency of this actuator is of the order of 100 kilohertz so the mirror is capable of being moved as rapidly as required by the motion of scanner arm 19. A control system is accordingly designed to drive the dither mirror 89 in synchronism with the scan wave form of FIG. 9A, e.g. with the wave form shown in FIG. 10A, to produce a compensated scan path such as is shown in FIG. 10B.

Transmission Microscope with Scan Motion Correction

A preferred embodiment incorporating the dither mirror, is the high speed tissue scanner of FIG. 3, modified to include dither mirror 89. The system scans tissue samples on microscope slides very quickly. The key to this ability is the micro lens objective which scans a 20 millimeter wide tissue sample at a rate of 100 scans per second. Red, green and blue laser light passes through the scanning objective lens, through the tissue sample, and into the integrating sphere. In the integrating sphere the fraction of light of each color transmitted by the sample is measured.

The micro objective lens 18, as an aspheric surface molded from one piece of glass, produces approximately a ½ micron diameter, diffraction limited spot at all three laser wavelengths. The tissue sample is therefore imaged in full color at a resolution of 1 micron. The lens in this particular embodiment may have a numerical aperture (NA) of 0.55 and a mass of only 0.205 gram.

The high scan speed, e.g. of 6.7 meters per second, results in a measurement of the transmission of each ½ micron diameter area (pixel) in 0.08 microseconds. The photosensors, amplifiers, and analog to digital converters which process each pixel are designed for this high speed.

The lens scans the tissue sample in an arc since it rotates in oscillatory fashion, about axis A which is, for example, 25.4 millimeters from the lens 18.

Using the position detector 43 of the oscillating structure, the electronic system reads off the actual position at each instant of data collection. The position signal is fed back as a servo control (not shown) to control the motor in accordance with a desired trajectory.

Other Uses of the Dither Feature

The dither or movable system can also be of advantage in enabling a stationary object to be scanned along multiple concertic arcs, by an arm that move at constant radius about a fixed axis relative to the object. A controlled increment of adjustment of the dither mirror between scans sweep can change the effective radius of the scan line on the object thus two or more scan lines can be produced for a given fixed position between the center of the rotation of the arm and the object.

Reflectance Microscope

The techniques that have been described in relation to a transmission microscope are readily applicable to a microscope that receives energy from the illuminated side e.g. a microscope based upon reflection or fluorescence.

The scanning arrangement of the reflectance microscope of FIG. 11 is like that of FIG. 3 except that dither mirror 89 (or in a non-dithered example, mirror 21) is located above armature 19 and a periscope is created via a hollowed shaft coupling.

To detect reflected light there is added to the FIG. 3 system a beam splitter 94 in the light path which passes 50% of the incident laser light, an interference filter 99, and an optical element 102 to direct the light on a sensor 95 such as a photo multiplier tube.

The reflective geometry may be used in such applications as biology where the sample is too thick to transmit significant light, or where it is inconvenient or impossible to make a very thin sample, as in metallurgy or the computer chip industry.

Direct Position Information for Lens-Carrying Arm

The embodiment of FIG. 12 is different from that of FIGS. 3 and 11 in that the angular position detector is directly associated with the moving arm 19, rather than with the motor 4.

A benefit of this construction is that position of the oscillating arm itself is determined at each instant of data collection. Exact position is thus used as the reference for data construction and for servo control of an inexpensive rotational motor.

An advantage of this embodiment is that the band width of the entire system can be quite small for a given speed performance, because imperfections in the dynamics are of no consequence, as the data reconstruction is performed by direct measurement of angular position, coming from the position sensor, the instantaneous radial distance from axis A to the beam on objective lens 18 being known. (This distance is constant in the case of a fixed reflector, or in the case of use of the dither mirror, the distance varies, but is known at all times). Band width of the position signal may be reduced by a sampling algorithm that samples a suitable number of points depending upon the accuracy required, between which each instantaneous position is extrapolated.

Fluorescence Detection

An application of great importance is the detection of fluorescent light stimulated by a laser beam delivered to the tissue, also illustrated by the system of FIG. 12.

For example, reading of fluorescence is done using conventional FITC labeling, by illuminating the object with light of about 494 nm and collecting the low intensity fluorescing radiation of about 518 nm, the emitted light being separated from the excitation light with filters. For this purpose, FIG. 12, a dichroic beam splitter 94 is inserted in the laser beam. The dichroic beam splitter is selected to preferentially transmit the incident laser light and reflect the slightly longer fluorescing wavelength. A major advantage of this system concerns the high numerical aperture, e.g. NA=0.68, of the on-axis micro objective lens 18 with or without its associated stationary lens or lenses 18b, shown in FIG. 13. A small part of the lens may be used to deliver the exciting illumination by departing from focus to generate a large spot diameter. The high numerical aperture then provides excellent collection of fluorescent light that is sent in all directions by the illuminated spot. The intensity of the fluorescing light in fluorescence microscopes may be ten orders of magnitude below the intensity of the incident laser light. The miniature lens not only collects the widely spread fluorescent light; due to it's high numerical aperture, it also converts the fluorescent light to a very nearly parallel beam. This alone, facilitates passage of the beam through the rotating arm, and, via the dichroic mirror, (in some cases in conjunction with a further collimating stationary lens, 18b, FIG. 13,) to the stationary detection area. One or more interference filters 99 are provided before the photo multiplier detector 95 to detect extremely weak levels of fluorescent light.

There are many different kinds of fluorescent objects for which a large number of picture elements is desired. In restriction mapping, DNA molecules are stretched out in nearly a straight line, and attacked by enzymes that break the molecules at various points, presenting a long line of molecular structure with breaks in it. The DNA endings can be made to fluoresce and, by inspection, one can learn the length of each unbroken segment, these lengths being useful to identify the segments. Reference is made for instance to the Human Genome News of July/August 1996, which is incorporated herein by reference. A discussion of the technique and a photograph of a particular chromosome stretched out and split into pieces is shown, with each piece fluorescing. The wide area scan capability of the present practical system, with its large number of picture elements, is very useful in this case. When the stretched out piece of DNA is generated, the scientist does not know precisely where it is located on the slide. A pool of liquid has been deposited and processed to produce an area of the order of 1 cm$^2$, which may contain a dozen or more DNA molecules at random locations. Finding the DNA molecules is not trivial. A large area scan, employing the present contribution, can accomplish this in an excellent way, to not only find the molecules, but to be able to present each one in total or at least a large length of it, to the scientist without the need to stitch together separate small pictures according to known techniques. As error may occur in stitching together several small pictures, one can not be confident that one has truly identified the broken segments of DNA, so redundant readings have been required to confirm the results. The wide field of view and large number of picture elements in the picture, achievable with the present techniques, is important for finding the DNA quickly and increasing the scientist's confidence, to speed the reading process.

Another use of fluorescence has to do with the techniques for DNA sequencing which result in regular rectangular arrays of sites at which hybridization reactions occur between a known DNA fragment and an unknown DNA, such as are produced by Affymetrix. These are applications in which the areas to be scanned may be very large because it is intended to have many different possible reactions available at sites distributed over one microscope slide. The ability to detect weak fluorescence is vital in this case because the fluorescing volumes at the sites on such DNA chips containing the reaction products are very small. Thus use of hybridization reactions detected by fluorescence is facilitated by the present system.

In other contexts, the fluorescence microscope principles are useful to read natural luminescence, without use of stimulating radiation. The confocal adaptation to be described can benefit the efficiency of such a technique.

Confocal Microscope

FIG. 12 also shows the general system of FIGS. 3 and 11 modified to serve as a limited rotation confocal microscope. In addition to the components previously shown, to achieve a confocal microscope, conditioning optical element 102 is employed which may be another aspheric lens or a lens of other design, in conjunction with a pin hole 103, provided in the focal plane of lens 102. The purpose of the pin hole and lens is to provide essentially that only light which originates in the focal plane on the sample is focused on the pinhole. Light originating at other heights or places is out of focus at the pinhole, only a small fraction of which passes through the pinhole. The light not desired is e.g., scattered laser light from beam dumps or ambient light. The photo multiplier tube 95 follows the pinhole so the amount of light collected due to the fluorescent source, relative to light from other sources, is maximized.

Examples of the Capabilities and Uses of Limited Rotation Micro Lens Scanners

A prime feature of the systems that have been described is the ability to produce a very large number of picture elements. In the case of a microscope slide 25 mm×75 mm, with a 1 micron spot size, 25,000×75,000 picture elements are defined. This is true for transmitted laser light, reflected laser light, fluorescent light or an optical task having nothing to do with collecting of images, for example, micro machining of a feature in the surface of a custom-integrated circuit or a photo mask, etc.

In micromachining, the scanning microscope is useful, e.g. to generate upon a photomask a density of 1 million picture elements per $cm^2$. Another application is in configuring custom-integrated circuits by selective ablation of a conductive layer, e.g. aluminum, that connects functional elements. The system selectively evaporates links so that a desired network of elements remains to define a circuit, such as in memory repair. The microscope assembly that delivers laser energy is also useful to read the surface being altered. A utilization of this feature is in semiconductor laser marking or laser trimming and memory repair, where there is a need to determine the location of the work piece relative to the optical system. Another use is in non-destructive edge sensing.

Certain basic contributions that have been described can be applied to different driving arrangements from those described. Numerous other embodiments are possible and are to be expected, employing one or more of the contributions that have been described.

What is claimed is:

1. A method of scanning by rotating an objective lens on a scan arm, comprising the acts of:
    supporting an objective lens on an oscillating support structure constructed for periodic scanning over biological material disposed on a substrate;
    scanning said objective lens in scanning arcs over said biological material disposed on said substrate while said objective lens being coupled to a light path partially extending over said oscillating support structure; said objective lens having a field of view of about twice its spot size; and
    employing a translation mechanism constructed for relative linear movement of said substrate and said support structure.

2. The method of claim 1 further comprising collecting by said objective lens fluorescent light emitted from said biological material.

3. The method of claim 2 wherein said collecting said fluorescent light comprises collecting fluorescent light emitted from DNA fragments included in said biological material.

4. The method of claim 3 further including, prior to said scanning, hybridizing said DNA fragments.

5. The method of claim 2 further comprising, prior to said collecting said fluorescent light, focusing by tilting said substrate in at least one direction.

6. The method of claim 1 wherein said scanning includes scanning a microscope slide supporting said biological material.

7. The method of claim 1 wherein said scanning includes scanning a DNA chip supporting said biological material.

8. The method of claim 1 wherein said scanning includes scanning a DNA chip supporting said biological material comprising DNA fragments.

9. The method of claim 8 further including, prior to said scanning, hybridizing said DNA fragments.

10. The method of claim 1 wherein said light path partially extending over said oscillating support structure includes a periscope assembly.

11. The method of claim 1 further comprising detecting radial position of said objective lens using a position detector.

12. The method of claim 1 wherein said scanning includes employing a galvanometer.

13. The method of claim 1 wherein said scanning includes employing a counterweight mounted on said support structure and arranged for balancing said objective lens.

14. A rotary scanning system producing arcuate scan motion comprising:
    an oscillating support structure, associated with a driver, constructed to support an objective lens for periodic scanning over biological material disposed on a substrate;
    said objective lens coupled to a light path partially extending over said oscillating support structure having a field of view of about twice its spot size;
    a translation mechanism constructed for relative linear movement said substrate and said support structure; and
    a data collection control arranged to time the data collection during the arcuate scan motion to align data collection points with rows of a predetermined raster grid to which the data is to be converted.

15. The scanning system of claim 14 including a data conversion system arranged to convert data to the raster grid by averaging for each raster point the value of each of the two data points in the row on either side of the raster point, the values weighted by their respective distances from the raster point in question.

16. The scanning system of claim 14 wherein said objective lens is arranged to collect fluorescent light emitted from said biological material.

17. The scanning system of claim 16 wherein said objective lens has a numerical aperture larger than 0.5.

18. The scanning system of claim 16 wherein said substrate includes a DNA chip arranged for hybridization of said biological material prior to scanning.

19. The scanning system of claim 16 wherein said substrate includes a DNA chip comprising said biological material arranged for DNA sequencing.

20. The scanning system of claim 14 wherein said oscillating support structure includes a periscope assembly arranged to provide said light path.

21. The scanning system of claim 14 further comprising a tilting mechanism constructed to tilt said substrate for focusing light passing through said objective lens.

22. The scanning system of claim 21 wherein said substrate includes a microscope slide comprising said biological material.

23. The scanning system of claim 21 wherein said substrate includes a DNA chip comprising said biological material.

24. The scanning system of claim 14 further comprising a position detector for detecting radial position of said objective lens.

25. The scanning system of claim 14 wherein said support structure includes a counterweight mounted for balancing said objective lens during said scanning.

26. An apparatus for scanning an objective lens on a scan arm, comprising:

means for supporting an objective lens on an oscillating support structure constructed for periodic scanning over biological material disposed on a substrate;

means for scanning said objective lens in scanning arcs over said biological material disposed on said substrate while said objective lens being coupled to a light path partially extending over said oscillating support structure; said objective lens having a field of view of about twice its spot size; and means for employing a translation mechanism constructed for relative linear movement of said substrate and said support structure.

27. The apparatus of claim 26 includes means for collecting fluorescent light emitted from said biological material.

28. The apparatus of claim 27 wherein said objective lens has a numerical aperture larger than 0.5.

29. The method of claim 28 wherein said objective lens has a numerical aperture larger than 0.5.

30. The apparatus of claim 27, wherein said substrate includes a DNA chip comprising said biological material arranged for hybridization prior to scanning.

31. The apparatus of claim 27, wherein said substrate includes a DNA chip comprising said biological material arranged for DNA sequencing.

32. The apparatus of claim 26 further comprising means for focusing by tilting said substrate in at least one direction.

33. The apparatus of claim 32, wherein said substrate includes a microscope slide comprising said biological material.

34. The apparatus of claim 32, wherein said substrate includes a DNA chip comprising said biological material.

35. The apparatus of claim 26 further comprising means for detecting radial position of said objective lens.

* * * * *